US011832802B2

(12) United States Patent
Swick et al.

(10) Patent No.: US 11,832,802 B2
(45) Date of Patent: Dec. 5, 2023

(54) BIOPSY DEVICE ARMING MECHANISM

(71) Applicant: HOLOGIC, INC., Marlborough, MA (US)

(72) Inventors: Zachary Stephen Swick, Westborough, MA (US); Rosario Friedman, Medford, MA (US); Brett Haarala, Framingham, MA (US); David Sauvageau, Westlake Village, CA (US); Donna Schulz Torres, Attleboro, MA (US)

(73) Assignee: HOLOGIC, INC., Marlborough, MA (US)

( * ) Notice: Subject to any disclaimer, the term of this patent is extended or adjusted under 35 U.S.C. 154(b) by 753 days.

(21) Appl. No.: 16/746,723

(22) Filed: Jan. 17, 2020

(65) Prior Publication Data

US 2020/0155128 A1 May 21, 2020

Related U.S. Application Data

(63) Continuation of application No. 15/414,966, filed on Jan. 25, 2017, now Pat. No. 10,537,311, which is a
(Continued)

(51) Int. Cl.
*A61B 10/02* (2006.01)

(52) U.S. Cl.
CPC .......... *A61B 10/02* (2013.01); *A61B 10/0275* (2013.01); *A61B 2010/0208* (2013.01); *A61B 2010/0225* (2013.01)

(58) Field of Classification Search
CPC .............. A61B 10/02; A61B 10/0275; A61B 2010/0208; A61B 2010/0225
See application file for complete search history.

(56) References Cited

U.S. PATENT DOCUMENTS

| 4,881,551 A | 11/1989 | Taylor |
| 4,924,878 A | 5/1990 | Nottke |

(Continued)

FOREIGN PATENT DOCUMENTS

| CA | 2506961 | 11/2005 |
| CA | 2532499 | 7/2006 |

(Continued)

OTHER PUBLICATIONS

English translation of DE 102009056143 A1 (cited as Foreign Patent Ref. No. 8 above), dated Jun. 1, 2011, 8 pages.
(Continued)

*Primary Examiner* — Daniel L Cerioni
(74) *Attorney, Agent, or Firm* — JONES ROBB, PLLC

(57) ABSTRACT

A biopsy device for percutaneous tissue removal includes an elongated housing having an operational axis, a stylet hub slidably mounted in the housing, where the stylet hub is movable relative to the housing between a proximal, armed position, and a distal, fired position, the stylet hub having a stylet strike, a cannula hub slidably mounted in the housing alongside the stylet hub, and a spring-biased arming member. The cannula hub is movable relative to the housing between a proximal, armed position, and a distal, fired position. The arming member is moveably mounted to the housing proximal of the respective stylet and cannula hubs, and configured for manually-actuated movement from a relaxed, extended position to a loaded, compressed position to define a compressive arming stroke. The biopsy device also includes an arming member biasing spring that restores the arming member from the compressed position to the extended position.

8 Claims, 31 Drawing Sheets

Related U.S. Application Data continuation of application No. 14/555,531, filed on Nov. 26, 2014, now Pat. No. 9,585,639.

(60) Provisional application No. 61/953,570, filed on Mar. 14, 2014, provisional application No. 61/909,234, filed on Nov. 26, 2013.

(56) References Cited

U.S. PATENT DOCUMENTS

| | | | |
|---|---|---|---|
| 4,958,625 | A | 9/1990 | Bates et al. |
| 5,183,054 | A | 2/1993 | Burkholder et al. |
| 5,195,533 | A | 3/1993 | Chin et al. |
| 5,392,790 | A * | 2/1995 | Kanner ............ A61B 10/0283 600/566 |
| 5,611,352 | A | 3/1997 | Chin et al. |
| 5,842,999 | A | 12/1998 | Pruitt et al. |
| 5,951,489 | A | 9/1999 | Bauer |
| 6,273,861 | B1 * | 8/2001 | Bates ............... A61B 10/0275 606/186 |
| 6,358,217 | B1 | 3/2002 | Bourassa |
| 8,343,070 | B2 | 1/2013 | Krueger |
| 2004/0097830 | A1 | 5/2004 | Cooke et al. |
| 2004/0097832 | A1 | 5/2004 | Adams et al. |
| 2004/0158172 | A1 | 8/2004 | Hancock |
| 2008/0319341 | A1 * | 12/2008 | Taylor ............... A61B 10/0275 600/567 |
| 2009/0299221 | A1 | 12/2009 | Bacon et al. |
| 2012/0253230 | A1 | 10/2012 | Williams et al. |
| 2012/0330186 | A1 | 12/2012 | Rhad et al. |
| 2013/0006143 | A1 | 1/2013 | Neoh |
| 2013/0023790 | A1 | 1/2013 | Schaeffer |

FOREIGN PATENT DOCUMENTS

| | | |
|---|---|---|
| DE | 202008011057 | 11/2008 |
| DE | 202008011058 | 11/2008 |
| DE | 102008038413 | 2/2010 |
| DE | 102008038414 | 2/2010 |
| DE | 102009056143 | 6/2011 |
| EP | 0207726 | 1/1987 |
| WO | 9639941 | 12/1996 |
| WO | 97352524 | 9/1997 |
| WO | 01/89389 | 11/2001 |
| WO | 2006116439 | 11/2006 |
| WO | 2011139876 | 11/2011 |
| WO | 2013/158072 | 10/2013 |

OTHER PUBLICATIONS

English translation of DE 202008011057 (cited as Foreign Patent Ref. No. 9 above), dated Nov. 20, 2008, 18 pages.

English translation of DE 202008011058 (cited as Foreign Patent Ref. No. 10 above), dated Nov. 20, 2008, 17 pages.

English translation of DE 102008038413 A1 (cited as Foreign Patent Ref. No. 11 above), dated Feb. 25, 2010, 18 pages.

PCT International Search Report and Written Opinion for International Appln. No. PCT/US2014/067786, Applicant Hologic, Inc., forms PCT/ISA/210 and 237, dated Feb. 25, 2015 (10 pages).

English Translation of DE 102008038414 (cited as Foreign Patent Ref. No. 3 above), dated Feb. 25, 2010, 11 pages.

Full Examination Report for AU Patent Appln. No. 2014354670, dated Jul. 25, 2018 (3 pages).

* cited by examiner

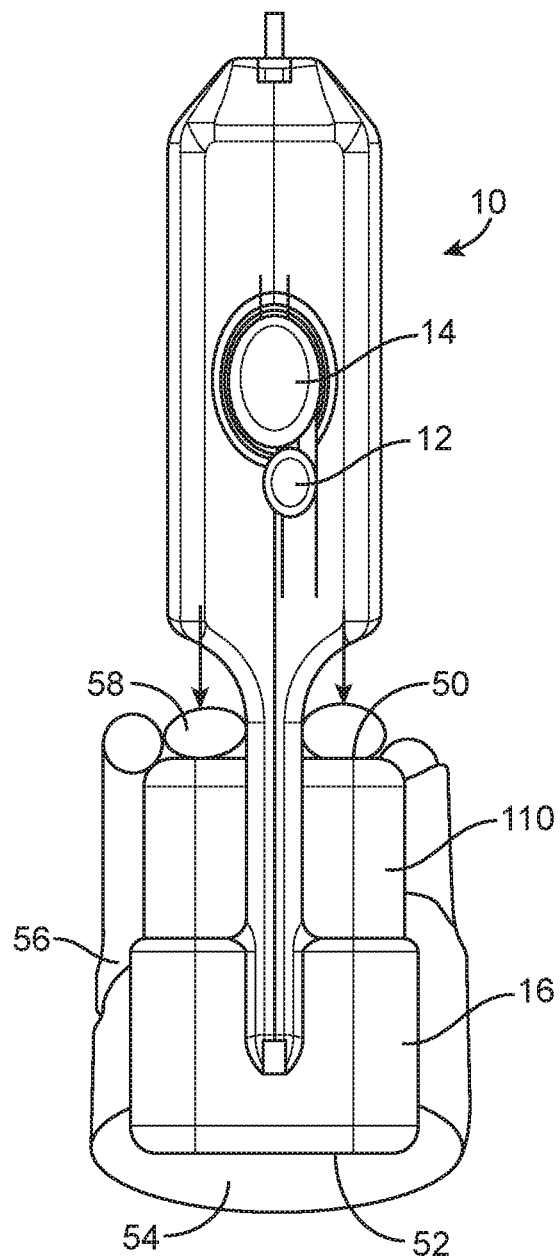
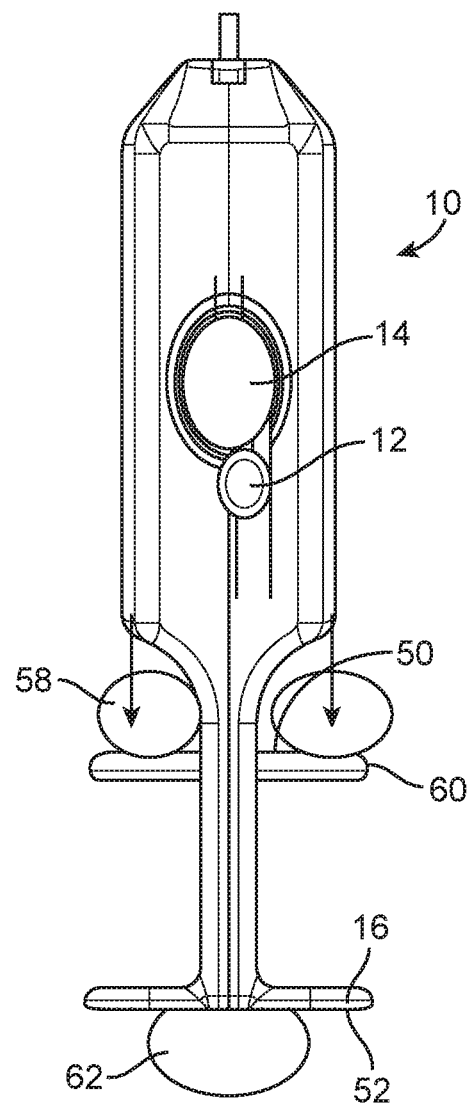
FIG. 1A
FIG. 1B

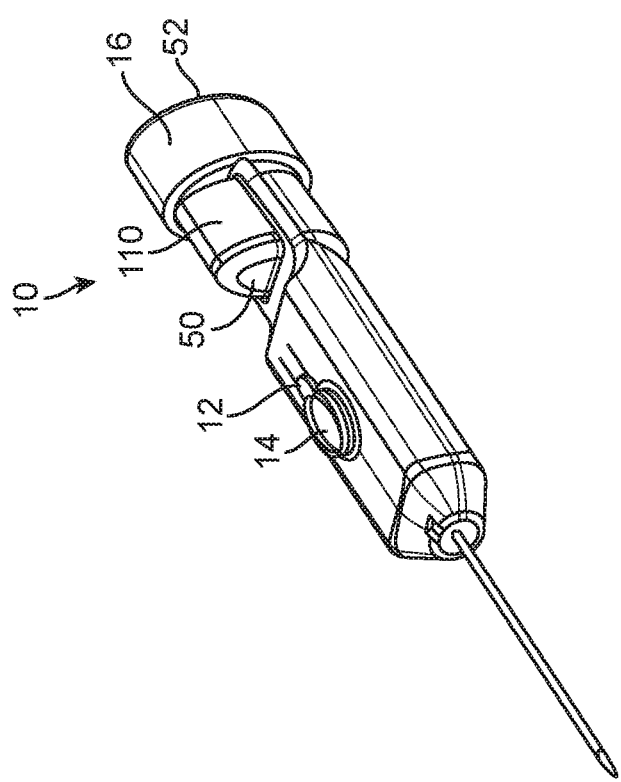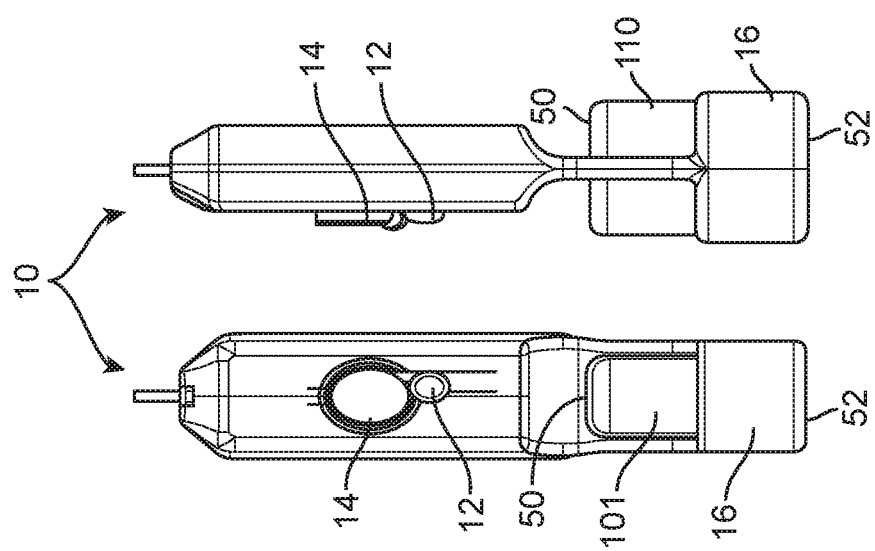
FIG. 4

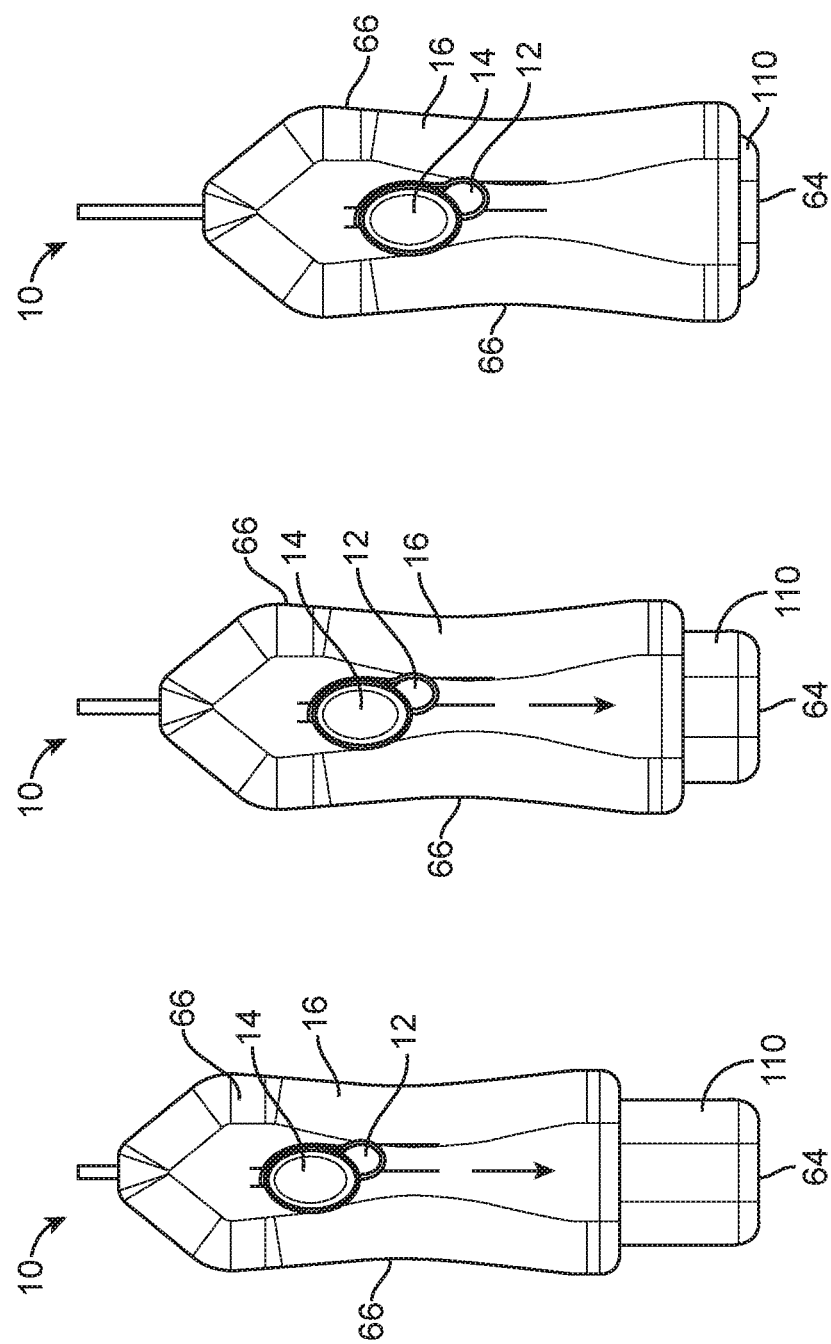

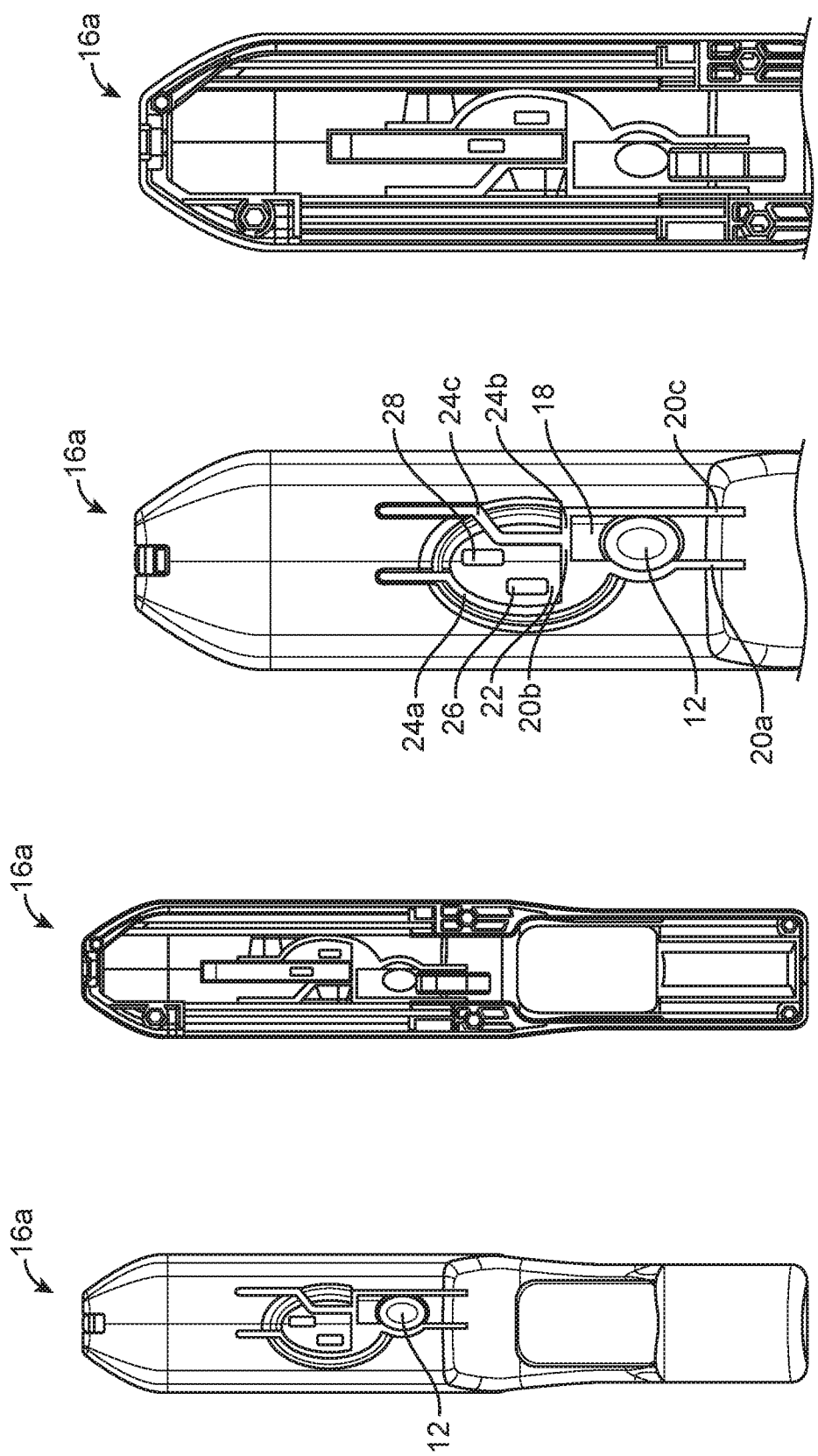

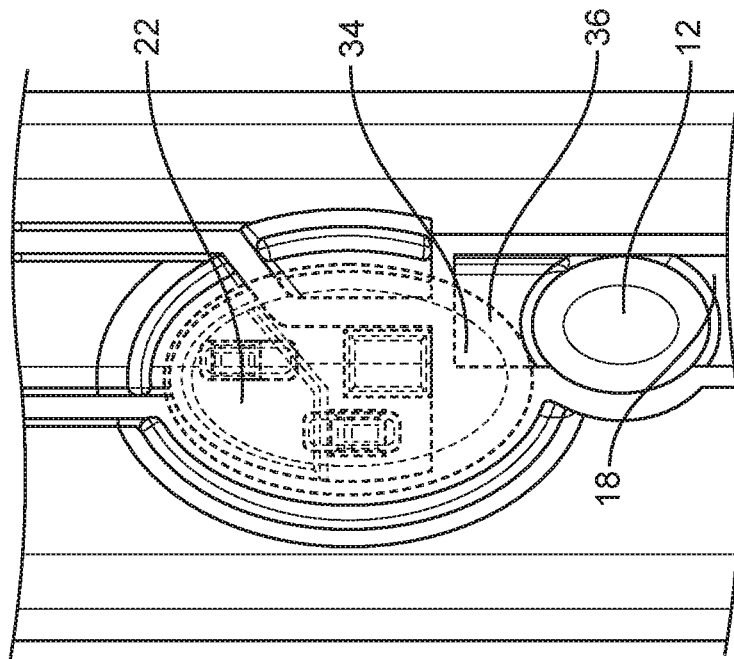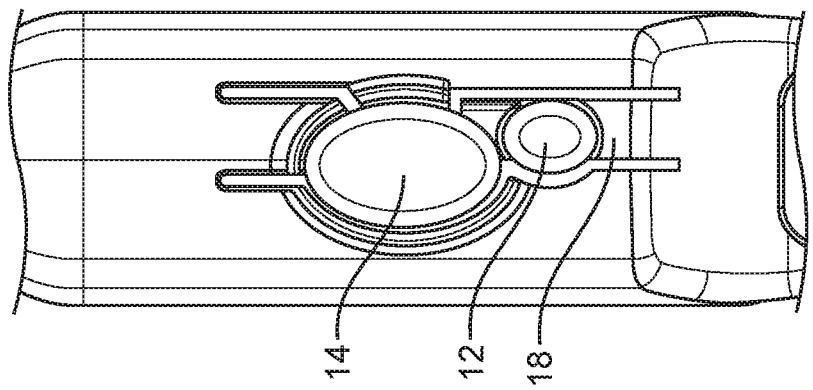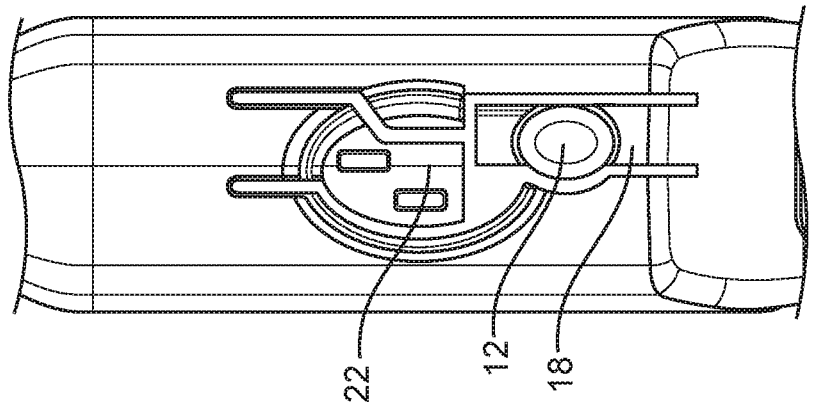

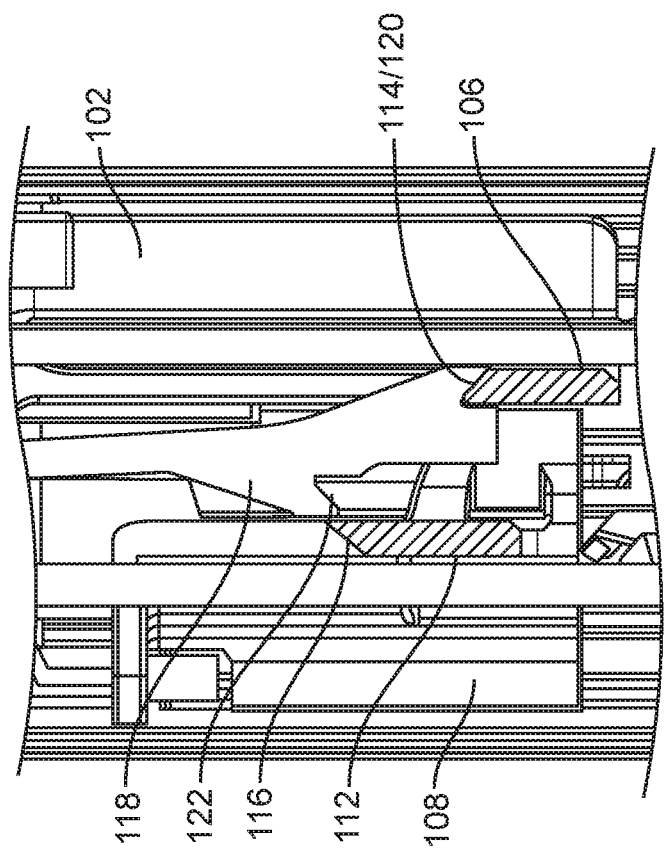
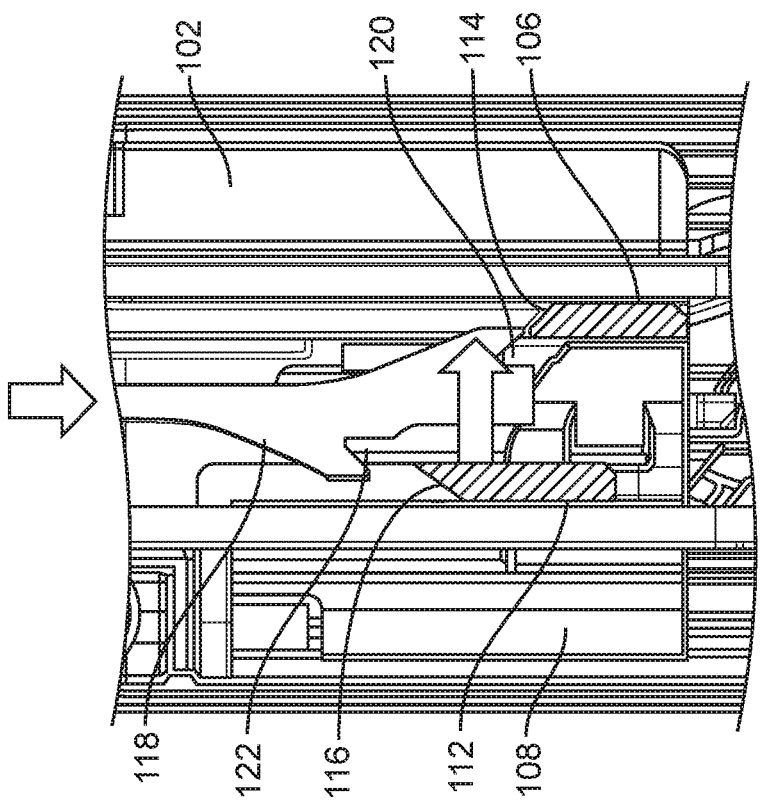

BIOPSY DEVICE ARMING MECHANISM

RELATED APPLICATION DATA

The present application is a continuation of pending U.S. patent application Ser. No. 15/414,966, filed Jan. 25, 2017, which is a continuation of U.S. patent application Ser. No. 14/555,531, filed Nov. 26, 2014, which claims the benefit under 35 U.S.C. § 119 to U.S. Provisional Application Ser. Nos. 61/953,570, filed Mar. 14, 2014, and 61/909,234, filed Nov. 26, 2013. The foregoing applications are hereby incorporated by reference into the present application in their entirety.

FIELD

The present disclosure generally relates to the field of tissue sampling and harvesting. More specifically, the disclosure relates to biopsy needle sets and devices.

BACKGROUND

In the practice of diagnostic medicine, it is often necessary or desirable to perform a biopsy, or to sample selected tissue from a living patient for medical evaluation. Cytological and histological studies of the biopsy sample can then be performed as an aid to the diagnosis and treatment of disease. Biopsies can be useful in diagnosing and treating various forms of cancer, as well as other diseases in which a localized area of affected tissue can be identified.

Biopsies are routinely performed on tissue using a needle set, which typically includes an inner needle/stylet with a pointed tip and an aperture/notch defined near its distal end. The stylet is slidably disposed within an outer cannula so that the notch can be alternately exposed or covered. Typically, a hub is connected to the proximal end of each needle. Such needle sets are used with or incorporated in various forms of biopsy devices, such as the single action and double action biopsy devices.

Currently, there are several soft tissue biopsy devices which are classified as Spring Loaded Core biopsy devices. These all share the characteristics of employing springs to create force and movement in needle cannulas axially to selectively remove a sample of the tissue. These devices are required to have the springs loaded, or armed, manually to compress and lock the springs in a compressed state to prepare for actuating the device. As the device is actuated the cannula moves rapidly forward to cut through tissue adjacent to the needle and contain it within the cannula until it is retrieved by the clinician.

Many of the current devices available are deficient in that they are difficult for users to arm and actuate the device and otherwise use the device due to ergonomic factors. For example it is highly desired for the user (usually a physician) to arm the device using a single hand since the other hand is frequently needed to hold other devices. Many current devices cannot be armed easily with a single hand. In addition, many users with smaller than average hands may not be able to arm devices designed for larger hands and also may not be able to arm the device with one hand. Many of the devices are designed so that a single finger is used to arm the device which can be difficult and to do because of the force required. Since the action of arming the device is the same action required to withdraw the outer cannula to access the excised tissue sample, the "arming motion" is done three times per sample (twice to arm the device and once to access the excised tissue sample). When the arming motion cannot be done with a single hand or without difficulty, it presents a significant challenge to the user during the medical procedure. Other devices require compression of elements with the fingers in an extended state which makes it difficult because it is not possible to generate as much force in an extended state as it is with the hand un-extended (e.g. with the hand held in a "C" shape). Some devices have arming features which spring forward and may hit and pinch parts of the hand or patient. In addition, it may be advantageous to arm the device using other surfaces besides the hand and use the muscles of the arm instead to more easily compress the springs.

Another issue is the inability to actuate (i.e., fire) the device easily in-use. Some devices have buttons that cannot be reached easily or require a motion that may disturb the placement of the device which may decrease accuracy of the tissue targeting. The actuation button can be difficult to depress due to the location of the button and/or the force required. In addition it is often desired to have the ability to acquire the tissue in two distinct steps for safety and efficacy reasons. In this case two or more buttons may be needed. Current devices have buttons that may be mistaken from each other due to similar shape and/or position. Current actuation buttons may be unintentionally depressed during handling because they are protruding and can be depressed with pressure coming from unintended contact with a hand surface and/or can be depressed easily with low force. A misfire can be unsafe or compromise the acquisition of tissue.

Current spring loaded core biopsy devices have spring loaded members which propel the needle element forward. The members are stopped when they impact a flat, rigid surface in the device casing by design. This controls the stroke and final position of the needle elements. Although this is effective in positioning and stopping the needle at the desired location, it results in the energy from the needle impact being converted to sound energy which is propagated to the casing of the device. This sound can be relatively loud and often startling to the patient. Most devices make a loud snap noise when actuated which can be startling to the patient who may already be in a distressed state due to the procedure. If the patient is startled not only is there the anxiety involved, but if the patient moves as a result of being startled, the safety and accuracy of the procedure may be affected.

Current devices may be configured so that the tissue aperture is oriented in a position that is not optimized for how the device is usually held. Many users will hold the device so that their hands are in a neutral position. In this position the thumb is on the side of the device in position to depress the button to actuate the device. When held in this position, the aperture opening is preferred to be facing up by many physicians; many devices have the aperture open to the horizontal plane while held in this position.

Needle axial concentricity to hand piece is yet another issue. Current devices have a needle which is asymmetric to the hand piece axis. This forces the operator to make an unnatural eccentric rotation of the wrist during positioning and acquisition of tissue to maintain the intended, centered position of the needle.

Arming feature design is still another issue. Current devices have arming features that protrude laterally external to the device. These features interfere with the patient's body during procedures causing discomfort and a limited range of motion.

Further, some current devices do not have a needle gauge size color indication for the operator to easily select or confirm proper needle size for the procedure.

SUMMARY

In one embodiment, a biopsy device for percutaneous tissue removal includes an elongated housing having an operational axis, a stylet hub slidably mounted in the housing, where the stylet hub is movable relative to the housing between a proximal, armed position, and a distal, fired position, the stylet hub having a stylet strike, a cannula hub slidably mounted in the housing alongside the stylet hub, and a spring-biased arming member. The cannula hub is movable relative to the housing between a proximal, armed position, and a distal, fired position. The arming member is moveably mounted to the housing proximal of the respective stylet and cannula hubs, and configured for manually-actuated movement from a relaxed, extended position to a loaded, compressed position to define a compressive arming stroke. The biopsy device also includes an arming member biasing spring that restores the arming member from the compressed position to the extended position.

In a single or multiple embodiments, the stylet hub has a stylet strike laterally offset from the operational axis in a first lateral direction, and the cannula hub has a cannula strike laterally offset from the operational axis in a second lateral direction, and proximal of the stylet strike, when the stylet hub and cannula hub are in the fired position. The biopsy device may also include a resilient arming shaft coupled to the arming member and extending along the operational axis. The resilient shaft is integrally formed with or otherwise attached to an arming shaft catch. The arming shaft catch, when the stylet hub and cannula hub are each in the fired positions, is configured to engage the cannula strike, upon a first compressive arming stroke, to thereby deflect the arming shaft catch away from the operational axis such that the arming shaft catch clears the stylet strike and moves the cannula hub to the armed position. The arming shaft catch is also configured to engage the stylet strike, upon a second compressive arming stroke, to move the stylet hub to the armed position. The arming shaft catch may include a first recess having an angled engagement surface configured to receive the cannula strike during the first compressive arming stroke, and a second recess having an angled engagement surface configured to receive and engage the stylet strike during the second arming stroke.

In a single or multiple embodiments, the biopsy device includes a stylet having a proximal end portion coupled to the stylet hub and a tissue piercing distal portion extending beyond the distal end of the housing, and a cannula having a proximal end portion coupled to the cannula hub. The stylet hub is biased by a stylet hub biasing spring toward a distal end of the housing for driving the stylet in a distal direction relative to the housing. The stylet hub may have a stylet hub catch for releasably retaining the stylet hub in the armed position. The cannula may be disposed coaxially around the stylet and may have an open-ended distal portion extending beyond the distal end of the housing. The cannula hub may be biased by a cannula hub biasing spring toward the distal end of the housing for driving the cannula over the stylet in a distal direction relative to the housing. The cannula hub may have a cannula hub catch for releasably retaining the cannula hub in the armed position.

In a single or multiple embodiments, the housing includes a first deflectable wall portion, and when the stylet hub is in the armed position, deflecting the first wall portion releases the stylet hub catch, causing the stylet hub spring to propel the stylet hub to the fired position. The housing may also include a second deflectable wall portion of the housing, and when the cannula hub is in the armed position, deflecting the second wall portion releases the cannula hub catch, causing the cannula hub spring to propel the cannula hub to the fired position. The second deflectable wall portion may be separated from the first deflectable wall portion so that deflection of the first wall portion does not release the cannula hub catch, and deflection of the second wall portion does not release the stylet hub catch. The biopsy device may include a first control pushbutton including or otherwise coupled to the first deflectable wall portion, and a second control pushbutton coupled to the housing at least partially over the first wall portion and at least partially over the second wall portion. In some embodiments, when the stylet hub and cannula hub are each in the armed position, depressing the second control button sequentially deflects the first and second wall portions, thereby sequentially releasing the stylet hub catch and the cannula hub catch, to thereby sequentially propel the respective stylet and cannula in the distal direction. The second control push button may be attached or otherwise fixed to the first wall portion, and spaced apart from the second wall portion by a gap, such that depressing the second control button substantially simultaneously deflects the first wall portion while not deflecting the second wall portion until the second control button is depressed through the gap to make contact with the second wall portion.

In a single or multiple embodiments, the housing has a distal portion and a proximal portion, where the respective stylet and cannula hubs are disposed within the distal portion of the housing, and the arming member is mounted to the proximal portion of the housing, the arming member having a surface configured to be depressed relative to the proximal portion of the housing to thereby move the arming member from the extended position into an interior of the proximal portion of the housing for completing a compressive arming stroke. The arming member surface may be depressed away from the distal portion of the housing for completing a compressive arming stroke. The arming member surface may be sized and configured for being manually depressed into the proximal portion of the housing using one or more fingers of a single hand. The housing may have a proximal end surface sized and configured for being retained against a palm of the single hand when the arming member surface is depressed, such that a compressive arming stroke can be made by backstopping the proximal end surface in the palm and squeezing the arming member into the proximal housing portion using the at least one finger, respectively, of the hand.

In a single or multiple embodiments, the arming member surface is depressed towards the distal portion of the housing for completing a compressive arming stroke. The arming member surface may include a distal end surface of the device, and the housing may be sized and configured for being grasped by a single hand, such that a compressive arming stroke can be made by grasping the housing using a single hand and pressing the proximal end of the housing against a rigid surface to thereby depress the arming member into the proximal housing portion.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 1A, 1B, 2A and 2B are top views of three embodiments of spring loaded core biopsy devices showing alternative arming motions.

FIG. 4 shows top, side and perspective views of another embodiment of a spring loaded core biopsy device.

FIG. 5 shows three top views of the embodiment depicted in FIG. 2 illustrating three stages in the arming motion.

FIGS. 11A-D are top views of the top half of a body of a spring loaded core biopsy device according to one embodiment.

FIGS. 13A-C are detailed top views of the body depicted in FIG. 11A showing first and second levers.

FIGS. 16 and 17A-C are detailed top longitudinal cross-sectional view of a spring loaded core biopsy device according to one embodiment at various steps of a first arming stroke.

DETAILED DESCRIPTION OF THE ILLUSTRATED EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, he terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

Figure 3:
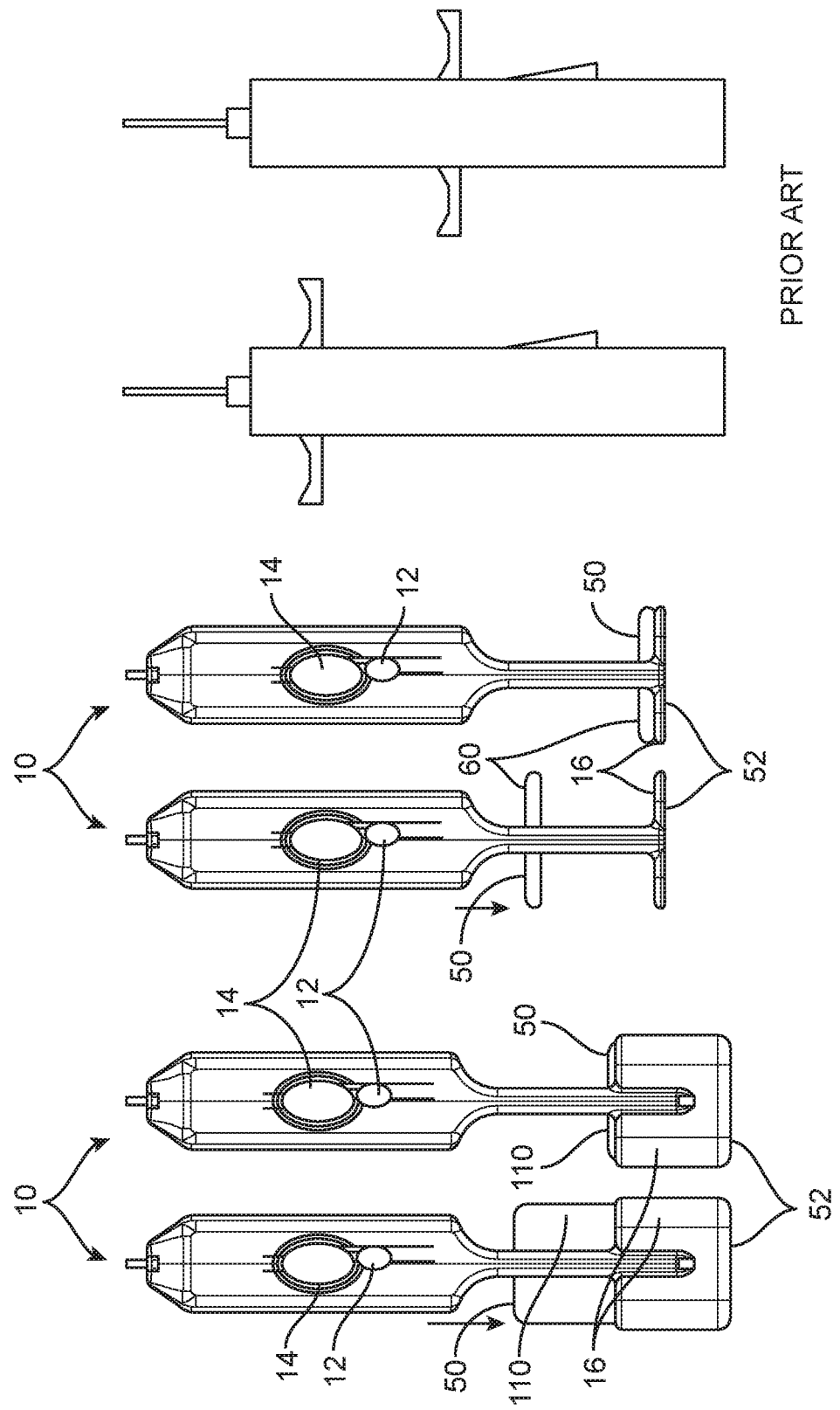
FIG. 3 is a top view of the two embodiments depicted in FIG. 1 and a schematic view of a prior art device showing the differences in arming ergonomics.

FIGS. 1A and 1B depict two spring loaded core biopsy devices 10 according to two related embodiments. The device 10 depicted in FIG. 1A includes a distally-facing arming button (or "arming member") 110 having a distal surface 50. The device 10 also includes a body 16 having a proximal surface 52. In order to arm the device 10, a user grasps the device 10 with the proximal surface 52 of the body in the palm 54 of a hand 56 and fingers 58 of the hand 56 on the distal surface 50 of the arming button 110. Then, the user squeezes the arming button 110 twice to arm the device 10 (as shown in FIG. 3). This motion can be accomplished in multiple ways, including but not limited to those shown in FIG. 1A.

The device 10 depicted in FIG. 1B includes an arming lever 60 having a distal surface 50, and a body 16 having a proximal surface 52. In order to arm the device 10, the user grasps the device 10 with a thumb 62 of a hand 56 on the proximal surface 52 of the body 16, and fingers 58 of the hand 56 on the distal surface 50 of the arming button 110. Then, the user squeezes the arming button 110 twice to arm the device 10 (as shown in FIG. 3). This motion can be accomplished in multiple ways, including but not limited to those shown in FIG. 1B.

Figure 2A:
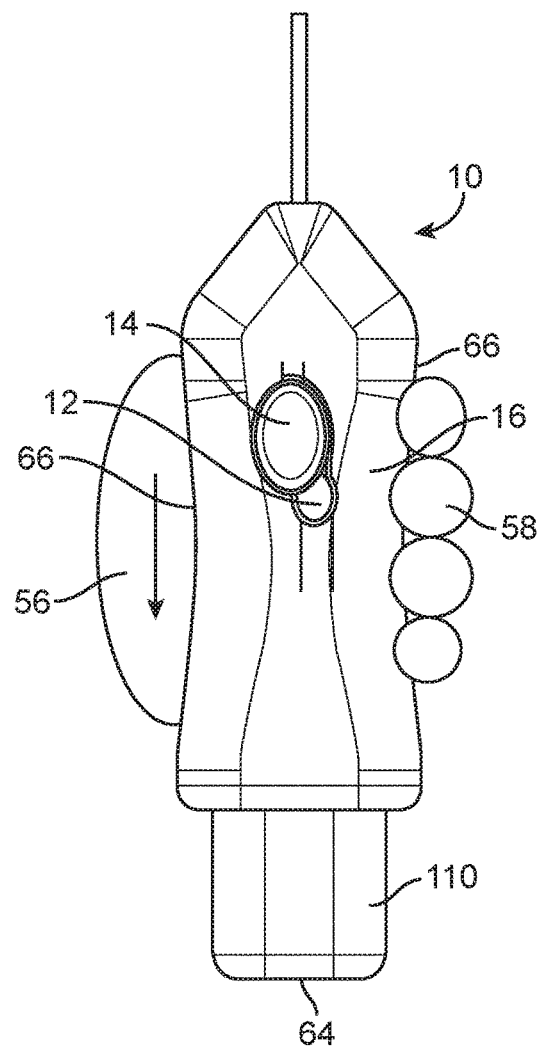
Figure 2B:
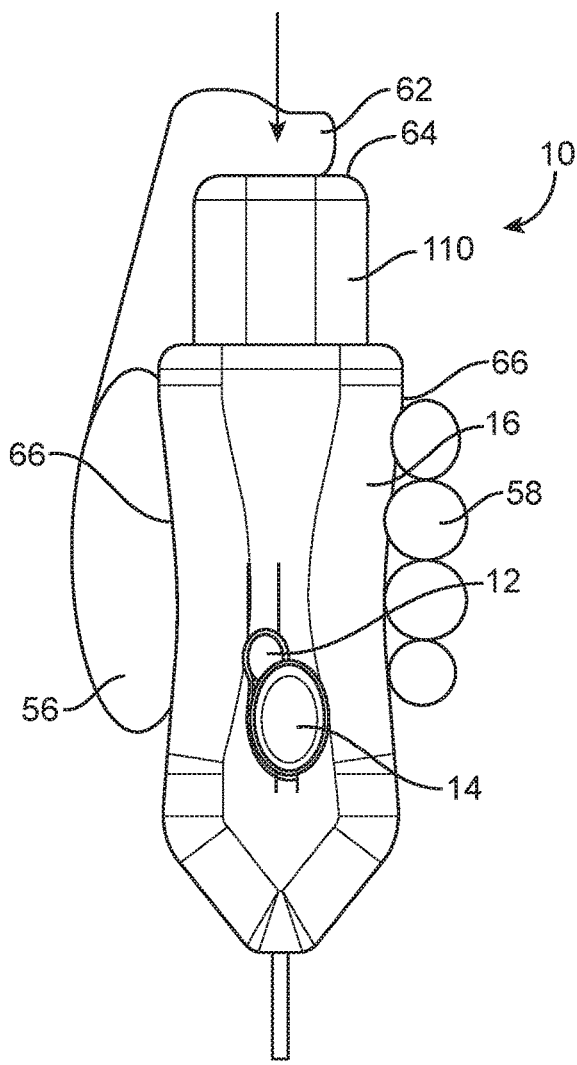

FIGS. 2A and 2B depict a spring loaded core biopsy device 10 according to another embodiment being armed using two different methods. The device 10 includes a proximally-facing arming button 110 having a proximal surface 64. The device 10 also includes a body 16 having two opposing longitudinal surfaces 66.

In the first method depicted in FIG. 2A, the user grasps the device 10 with fingers 58 and palm 54 of a hand on respective opposing longitudinal surfaces 66. The user holds the device 10 in either an "up" or "down" position relative to the user's thumb 62 (i.e., with the arming button 110 on respective different or same side of the user's hand from the user's thumb 62). FIG. 2A depicts a user holding a device 10 in an "up" position. With a firm grip on the device 10, the user presses the proximal surface 64 of the arming button 110 against any supported (preferably flat) surface (not shown) to squeeze the arming button 110 twice to arm the device 10. The user can press the arming button 110 against the supported surface using any arm motion including up, down or sideways.

In the second method depicted in FIG. 2B, the user grasps the device 10 with fingers 58 and palm 54 of a hand on respective opposing longitudinal surfaces 66. The user holds the device 10 in a "down" position relative to the user's thumb 62. The user presses the proximal surface 64 of the arming button 110 using the thumb 62 of the hand 56 in which the device 10 is held to squeeze the arming button 110 twice to arm the device 10.

FIG. 4 depicts a spring loaded core biopsy device 10 is similar to the device 10 depicted in FIG. 1A. The difference between the devices 10 depicted in FIGS. 4 and 1A is that the arming button 110 is rotated 90 degrees in the device 10 depicted in FIG. 4. Rotation of the arming button 110 improves the fit of the proximal end of the device 10 in the palm 54 because the depth of the arming button 110 is narrower than its width. This rotation of the arming button 110 may also be applied to the devices 10 depicted in FIGS. 1B, 2A and 2B.

In the embodiments depicted in FIGS. 1A, 1B, 2A, 2B and 4, the inner needle/stylet can be fired independently of the outer cannula by depressing/actuating the smaller button 12, which is located toward the more proximal end of the device 10, after which the outer cannula can be advanced by pressing the larger, more distally located button 14 to excise tissue prolapsing into the aperture in the inner needle (described below). Alternatively, both the inner needle and the outer cannula can be fired sequentially by only depressing the larger, more distal button 14 (described below). To recover samples from the aperture, the user depresses/actuates the arming button 110 a single time to expose the aperture and arm the outer cannula. To perform further biopsies, the arming button 110 is depressed/actuated once more, and the device 10 is fully armed again and ready to acquire tissue.

Single Handed Usability:

In the device 10 depicted in FIG. 1A, the arming button 110 is adjacent to the proximal end of the device 10 and employs multiple fingers 58. Therefore, the device 10 can be armed or the cannula can be retracted to expose tissue in the aperture with one hand 56 in a non-extended position using a compressive arming stroke, even for users with small hands. This is in contrast to an extending arming stroke, which requires two hands. The device 10 is symmetric in two planes (two perpendicular planes passing through the longitudinal axis of the device 10) for easy use with both hands 56 and for easier access of the fingers 58 to the arming button 110. It can be easily transitioned from arming to acquiring/firing positions. The reach required for arming this device 10 is only 2.25 or 1.3 inches compared to 4 inches or more of the existing devices, as shown in FIG. 3. This difference is significant in relation to the span of the hand 56. This allows the device 10 to be armed with a single hand 56 more easily because of improved control of the hand 56 in the position shown in FIG. 1A, as well as the increased force/strength generated by a hand 56 in this position. The features of the device 10 depicted in FIG. 1A that facilitate single handed usability are also present in the devices 10 depicted in FIGS. 1B and 4.

In the device 10 depicted in FIGS. 2A and 2B, the arming button 110 is at the proximal end of the device 10, and is compressed into the body 16 of the device 10 to arm the device 10, as shown in FIG. 5. Therefore, the device 10 can be armed by grasping the body 16 of the device 10 and pressing downward onto a supported surface (such as a table, or the physician's leg; FIG. 2A), or by flipping the device 10 upside down and depressing the arming button 110 with the thumb 62 (FIG. 2B). Pressing downward with the muscles of the arm and shoulder as opposed to the much smaller muscles in the hand 56 gives the physician a mechanical advantage, making the device 10 significantly easier to arm than existing devices. Using the device 10 this way, no shifting of the hand is necessary between arming and firing actions. Little to no reach (in terms of fingers) is required for the user to arm the device 10. If the physician chooses to arm using the thumb 62, the thumb 62 must reach approximately one inch to arm the device 10.

Actuating/Firing the Device:

The devices depicted in FIGS. 1A, 1B, 2A, 2B and 4 are actuated by depressing one or two buttons 12, 14 in succession in order to release internal components. As can be seen in FIGS. 13A-C and 15, the buttons 12, 14 are depressed normal to the longitudinal axis of the device 10 and in locations that are adjacent to fingers 58 and thumbs 62 of a hand 56 when the device 10 is held by the hand 56 in a natural position. Depressing the buttons normal to the longitudinal axis also minimizes the amount that the depressing motion will disturb the device 10 location. FIGS. 13A-C and 15 also show the distinct size difference between the two buttons 12, 14 that serves as a non-visual indicator of button function, as well as the raised case around the larger firing button 12 that reduces accidental actuation. The actuation mechanisms for the devices 10 depicted in FIGS. 1A, 1B, 2A, 2B and 4 are the same.

Noise Reduction:

The device 10 depicted in FIGS. 1A, 1B, and 4 include features that reduce the sound accompanying firing of the devices. These features include use of contacting surfaces that are not perpendicular to the axis of travel of the needle and cannula, surfaces with more contact area, flexible ribs, and sound energy absorbing materials in the body 16 to muffle the sound, prevent propagation of the energy to the casing and to dampen or absorb the energy, as shown in FIGS. 6A-D and described below.

Instead of two surfaces perpendicular to the axis of travel of the needle and cannula contacting to stop distal travel of the needle and cannula, mating surfaces with conical, angled, hemispherical, parabolic or other non-planar shape can be used. These shapes increase the surface area and also reflect the energy of impact away from the casing, resulting in less sound from the casing.

Also, energy absorbing material including elastomeric, porous, foam, and polymers with additives that absorb energy can be used to prevent loud sounds from being produced by the device. These materials can be disposed in the device 10 so as to cushion the moving parts. Alternatively, the energy absorbing material can absorb sound energy without coming in to contact with the moving parts. The absorbing materials can be used with or without the non-perpendicular surfaces described above.

Figure 6A:
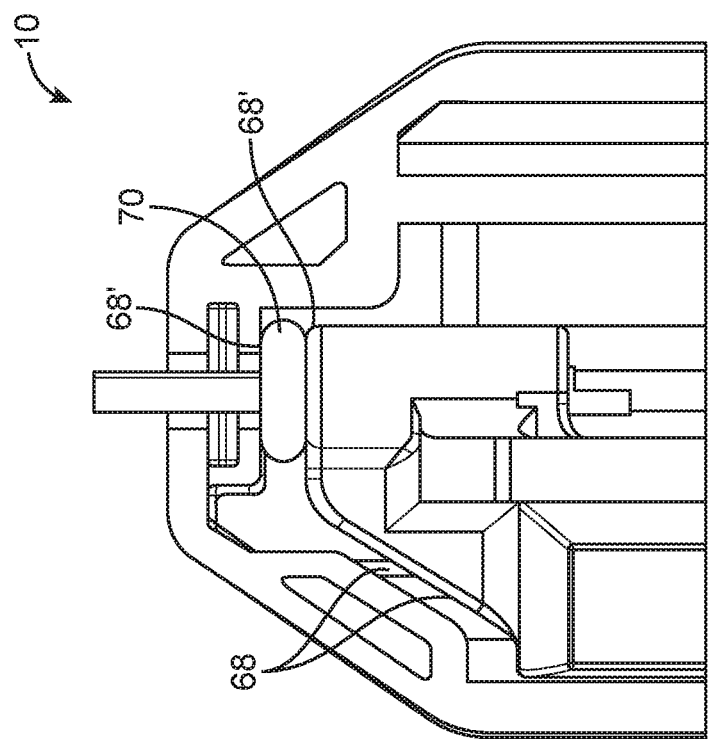
FIGS. 6A-D are detailed top longitudinal cross-sectional (FIGS. 6A-C) and perspective (FIG. 6D) views of an embodiment of a spring loaded core biopsy device.
Figure 6B:
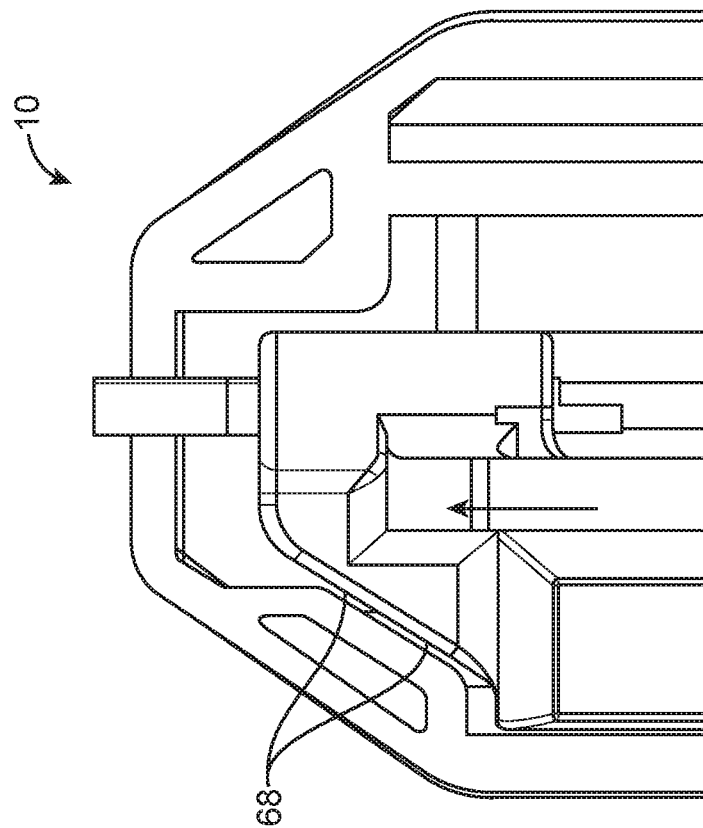

The noise produced by the actuation of the biopsy device 10 can be minimized using multiple features including, but not limited to, contact surface geometry, bumpers, and materials. Case materials can be chosen that will dampen a significant portion of the noise produced by impact of internal parts of the device 10. Bumpers can be disposed on impact surfaces to further dampen the sound produced during operations. FIG. 6A shows an example of how impact surfaces 68 that are angled with relation to the motion of impact (i.e., axis of travel of the needle and cannula) can reduce the amplitude of the transmitted impact force and subsequent noise. As shown in FIG. 6B, a bumper 70 could be placed adjacent an impact surface 68 to minimize sound generated by impact forces. In fact, adding a bumper 70 can generate new impact surfaces 68' that impact the bumper 70 instead of each other.

Figure 6C:
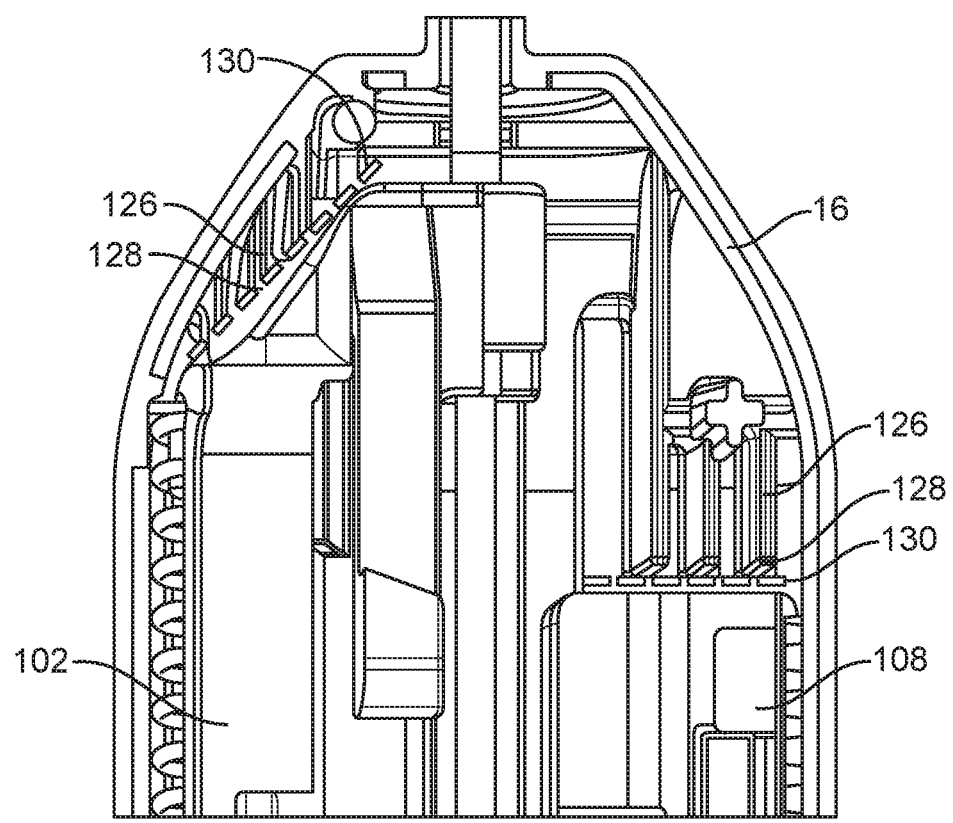
Figure 6D:
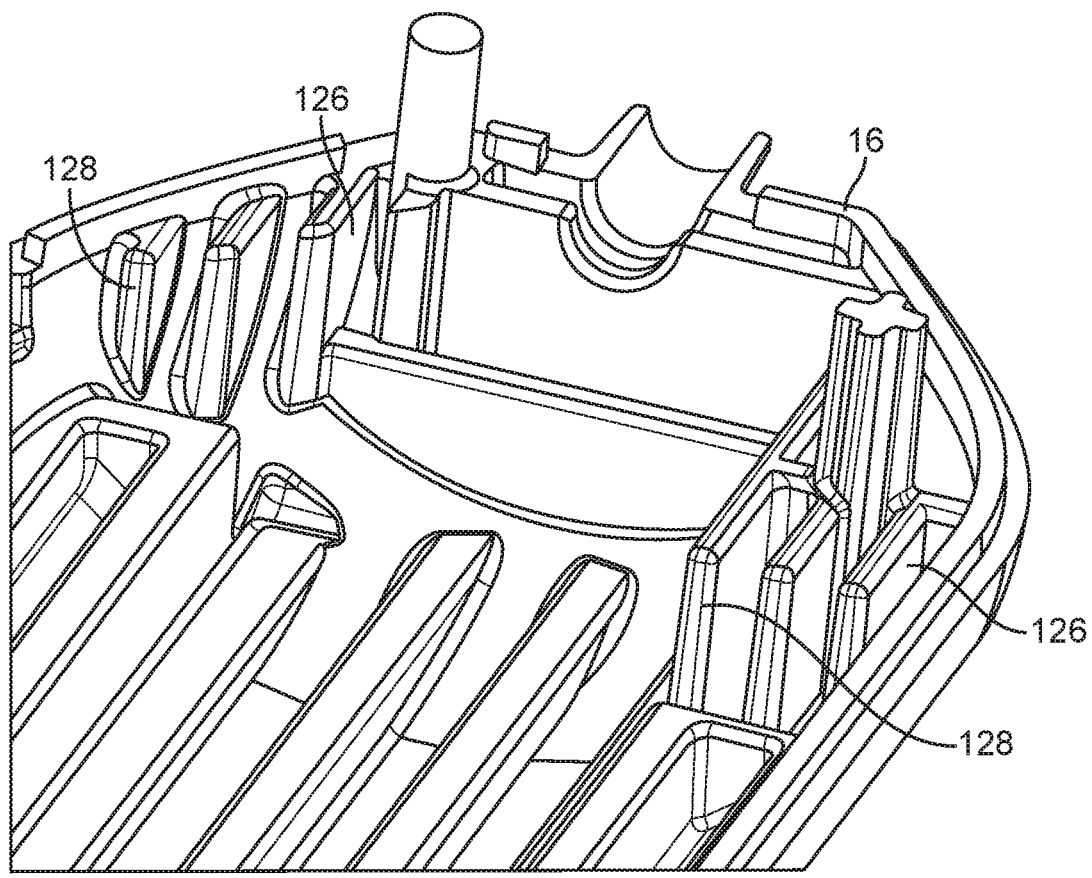

FIGS. 6C and 6D depict an embodiment of a biopsy device 10, and illustrate noise reduction features similar to those in the embodiment depicted in FIG. 6A. In this embodiment, the interior of the biopsy device body 16 includes flexible ribs 126 configured to stop the respective distal motion of the cannula carriage/hub 102 and the needle carriage/hub 108. The ribs can be made from energy absorbing materials, including elastomers, porous materials, foam, and polymers with additives.

The ribs 126 have a narrow cross-section. Therefore, they bend under axial stress (from the distal motion of the cannula carriage/hub 102 and the needle carriage/hub 108), thereby absorbing some of the energy generated by the impact of the cannula carriage/hub 102 on the proximal ends 128 of the ribs 126 at the point of impact 130. Absorbing the energy of impact reduces the sound generated by that impact. The ribs 126 also prevent propagation of the energy to the outside of the body 16, further reducing the sound generated by the impact. In addition, the ribs 126 configured to stop the distal motion of the cannula carriage/hub 102 define a point of impact 130 that is not perpendicular to the axis of travel, thereby further absorbing the energy and reducing the sound of impact. Although FIGS. 6C and 6D depict only one half of the body 16, both the top and bottom halves of the body 16 can include ribs 126.

In alternative embodiments, such as those depicted in FIGS. 2A, 2B and 5, the device 10 can include one or more tethers (not shown) to stop the motion of the firing needle and/or cannula. Such tethers can include braided wire, a recoiling elongate member and a dashpot.

Aperture Orientation:

It may be desirable for the aperture to face a direction other than the side of the device 10 with the firing buttons 12, 14. This direction can be optimized based on the specific design for physician comfort or preference. The device 10 can include an intuitive indication of the direction of the aperture on the body 16 of the device 10.

Figures 7A, 7B:
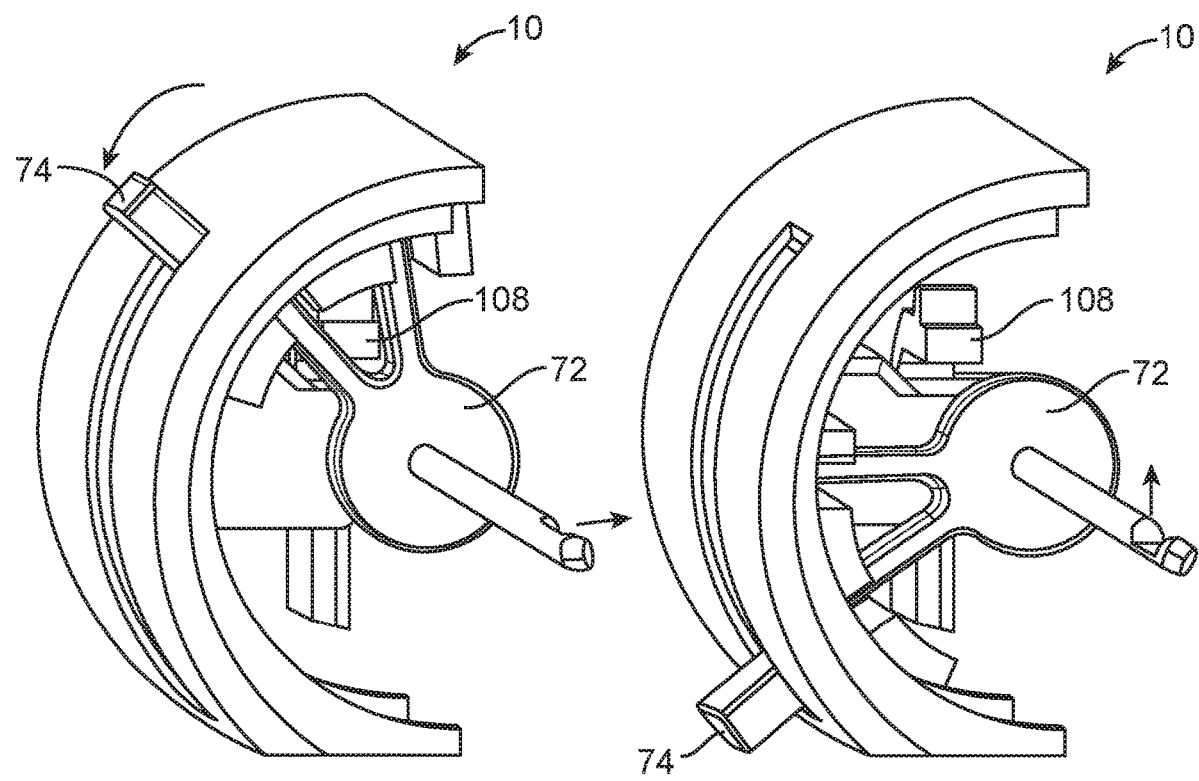
FIGS. 7A-B are detailed perspective views of select components of an embodiment of a spring loaded core biopsy device, with other components omitted to show a rotatable aperture orientation control mechanism.

The device 10 can also include a needle that rotates within the case of the device 10 to give the physician his or her choice of aperture orientations. FIGS. 7A and 7B depict a mechanism that would allow the physician to change the orientation of the needle aperture. This mechanism employs a rotatable collar 72 inside the device 10 that houses the linear guides for the needle hub 108. The physician can rotate this collar 72 by means of a small exterior protrusion 74, lever, or sliding button. Springs may be attached to the needle hub 108 that will drive the needle forward for firing, but will not restrict the needles rotational alignment.

Figure 8A:
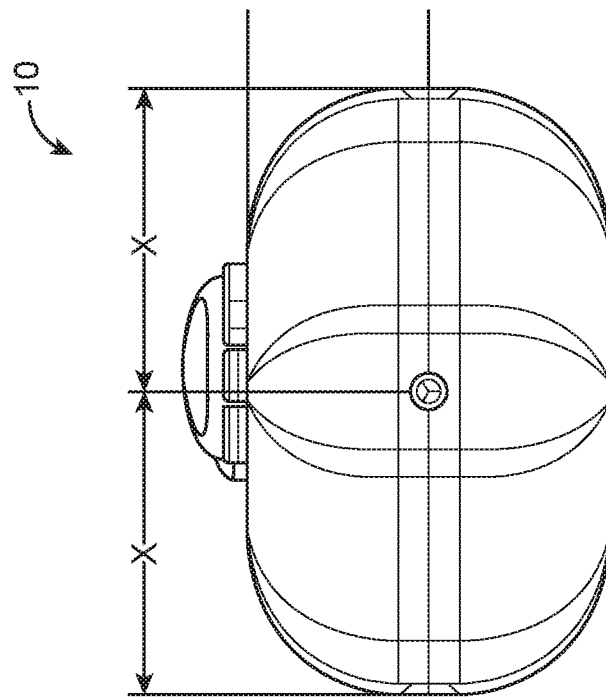
FIGS. 8A-B are end views of the embodiments depicted in FIGS. 1 and 2.
Figure 8B:
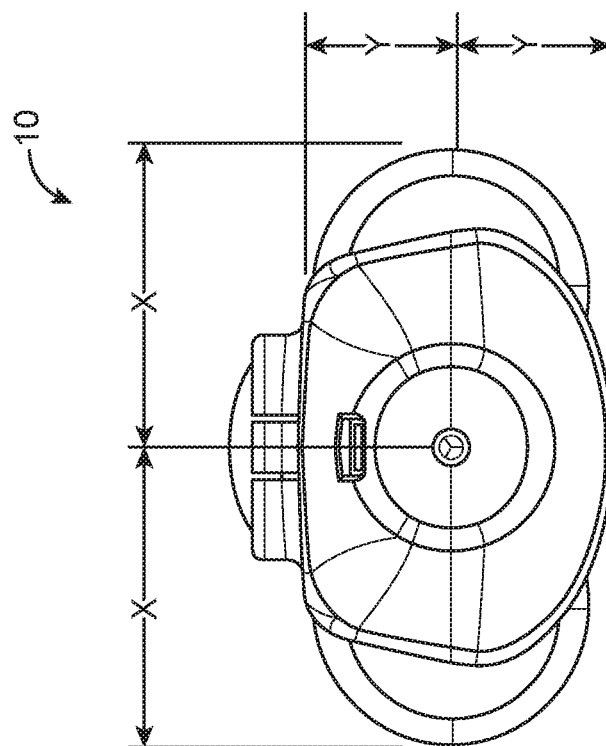

Axial Needle Concentricity:

The needle is centered within the device outer case in both the height and width directions in order to facilitate ease of the physician rotating the device around the needle axis while maintain the position of the needle tip relative to a stationary target. This will allow the clinician to intuitively rotate the device for desired tissue acquisition aperture location while minimizing unwanted needle motion during targeting. FIGS. 8A and 8B respectively show the embodiments depicted in FIGS. 1A-1B and 2A-2B from the distal end for visualization of needle concentricity relative to the outer case of the device 10.

Arming Feature Design:

The surfaces of the features employed by the user to arm the internal mechanism are within the envelope of the outer case when viewed from an end of the device 10, as shown in FIGS. 8A and 8B. Because the devices 10 do not include features that extend beyond the axial envelope of the outer case, the arming features of the devices will not unintentionally contact a patient's body during a biopsy. Known devices, on the other hand, often have wings or arms that protrude from the device near the biopsy site surface on the patient, and can therefore unintentionally contact the patient's body during a biopsy. Such unintentional contact can be painful or uncomfortable for the patient, and can be a nuisance for the physician attempting to place the device accurately. Eliminating features that could contact the patient results in a more comfortable experience for both the patient and the physician during certain procedures with difficult to reach lesions.

Distal Needle Support:

Adding inserts to the case mold or a small spacer to the assembly can create a more precise fit between the needle and the case by minimizing empty space around the needle at the most distal end of the case. This minimizes movement of the needle relative to the body of the device, thereby increasing the accuracy of the needle trajectory when fired. With a large amount of empty space between the needle and the case, the needle can be shifted from the intended axis of trajectory by resistance from the tissue. Movement of the needle can also render it more difficult to advance through tissue manually when targeting a lesion (before firing the needle).

Figure 9:
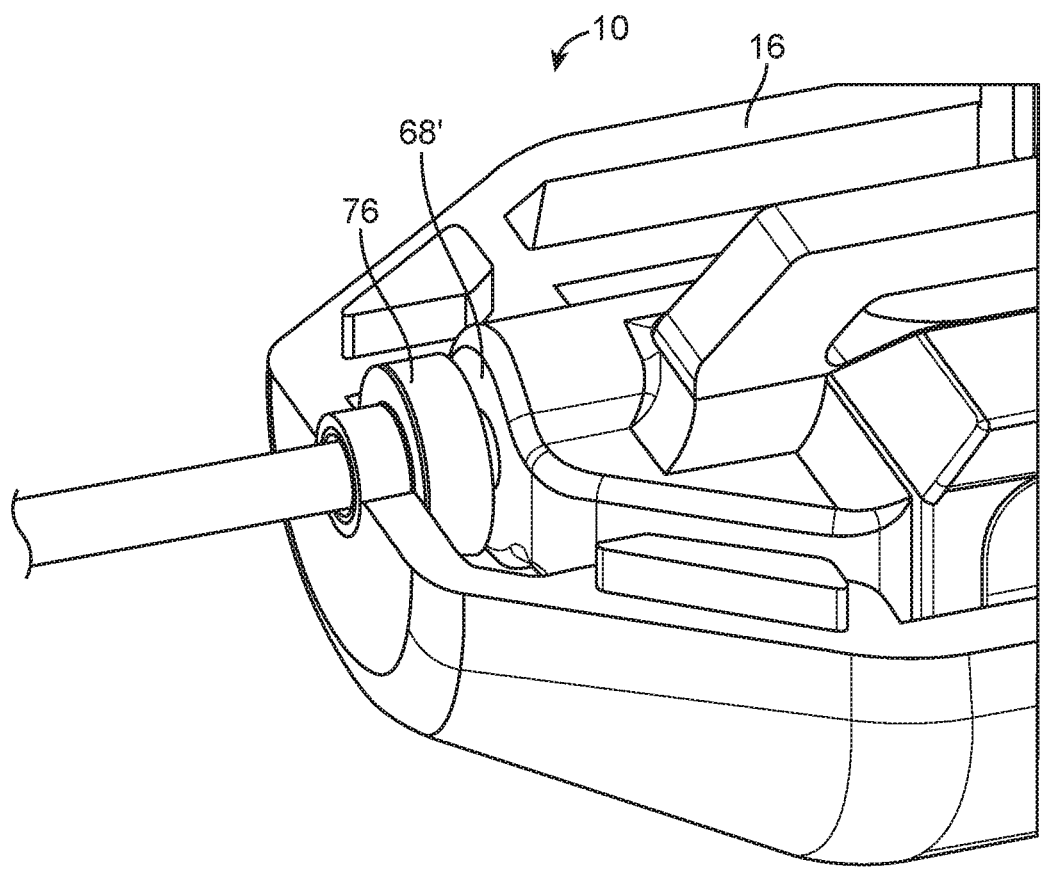
FIG. 9 is a perspective view of an embodiment of a spring loaded core biopsy device, with the top of the body omitted for clarity.

FIG. 9 show an insert/spacer 76 that includes an integrated noise reducing bumper component to serve a dual purpose. Additionally, a spacer could extend past the most distal end of the case (not shown) and perform a tertiary function as a feature for the needle sheath to press fit onto. This feature ensures that the sheath does not unintentionally slip off of the needle.

Figure 10:
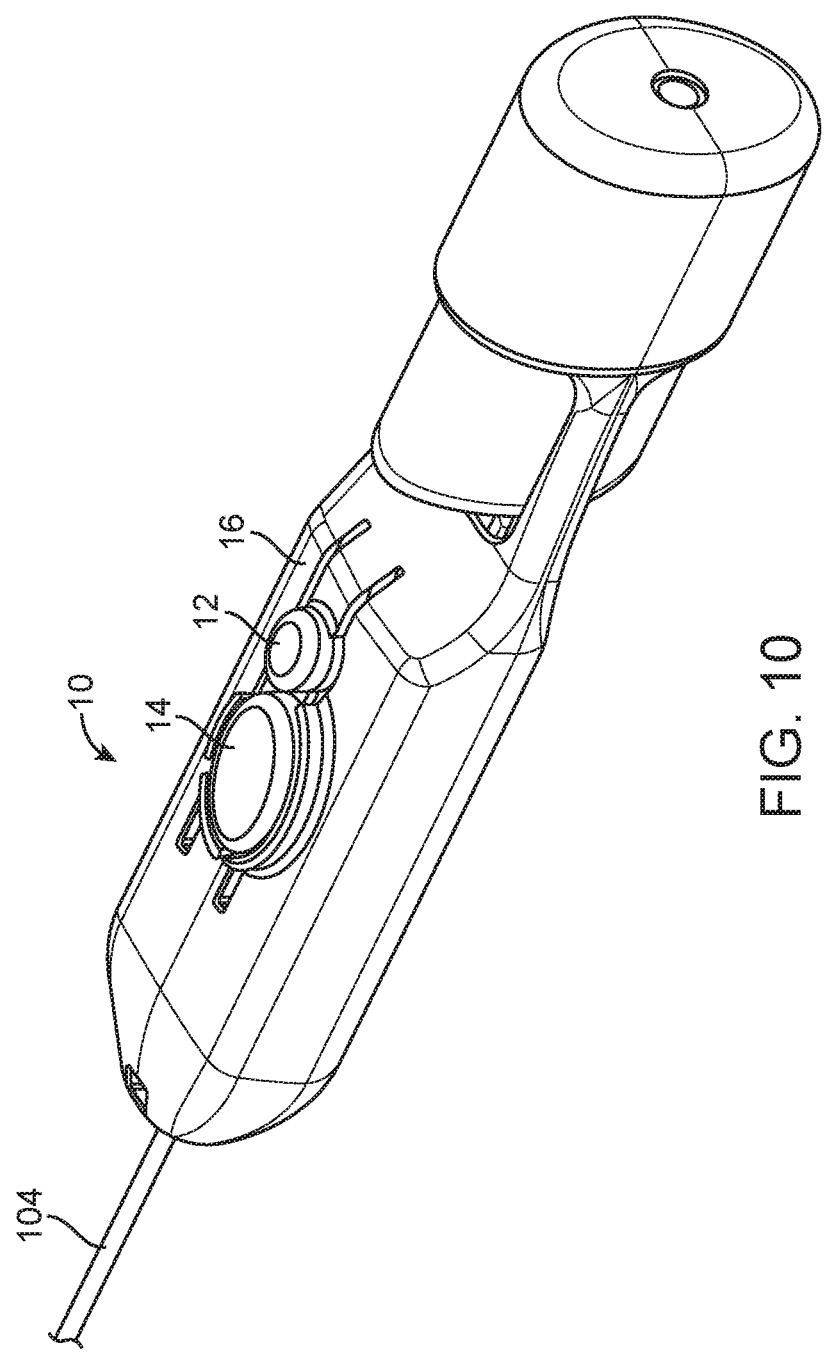
FIG. 10 is a perspective view of the embodiment depicted in FIG. 4, with the distal end of the needle omitted for clarity.

Actuation/Firing Mechanisms:

FIGS. 10-15 depict an embodiment of a biopsy device 10, and illustrate the actuation/firing buttons 12, 14 for firing the inner needle (not shown) and the outer cannula 104. The embodiment depicted in FIGS. 10-15 may share some components or process steps with or be identical to other embodiments described above. FIG. 10 depicts a biopsy device 10 having a smaller firing button 12 and a larger firing button 14. The smaller firing button 12 is located more proximally on the device body 16 than the larger firing button 14.

FIGS. 11A-D depict a top half 16a of a biopsy device body 16. FIGS. 11A and 11C are top views of the top half 16a of the biopsy device body 16, showing the exterior thereof. FIGS. 11B and 11D are bottom views of the top half 16a of the biopsy device body 16, showing the interior thereof. For instance, the top half 16a of the biopsy device body 16 can snap together with a bottom half of the biopsy device body 16 (not shown) to form a biopsy device body 16. FIGS. 11C and 11D are enlarged views of the distal portions of biopsy device body top half 16a shown in FIGS. 11A and 11B to better illustrate the details related to the firing buttons 12, 14.

As shown in FIG. 11C, the smaller firing button 12 is formed from the top half 16a of the biopsy device body 16. The smaller firing button 12 is formed on a first lever 18 defined by three slots 20a, 20b and 20c in the top half 16a of the biopsy device body 16. Because of the three slots 20a, 20b, and 20c, the first lever 18 is pivotally movable into and out of the plane defined by a top surface of the body top half 16a.

Also shown in FIG. 11C, is a second lever 22 defined by three slots 24a, 24b and 24c in the top half 16a of the biopsy device body 16. The second lever 22, includes first and second openings 26, 28, which facilitate mechanical coupling of the larger firing button 14 (see FIG. 12B) to the second lever 22. Because of the three slots 24a, 24b, and 24c, the second lever 22 is also pivotally movable into and out of the plane defined by a top surface of the body top half 16a.

Figure 12A:
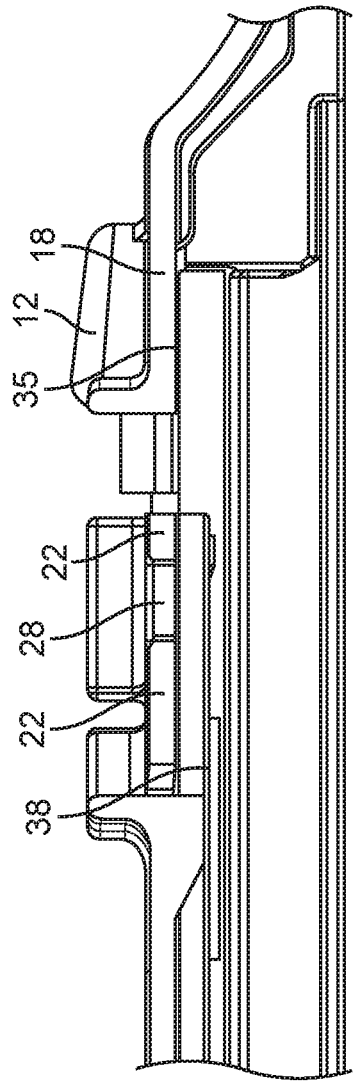
FIGS. 12A-B are detailed side longitudinal cross-sectional views of the body depicted in FIG. 11A. A button is attached to the body in FIG. 12B.
Figure 12B:
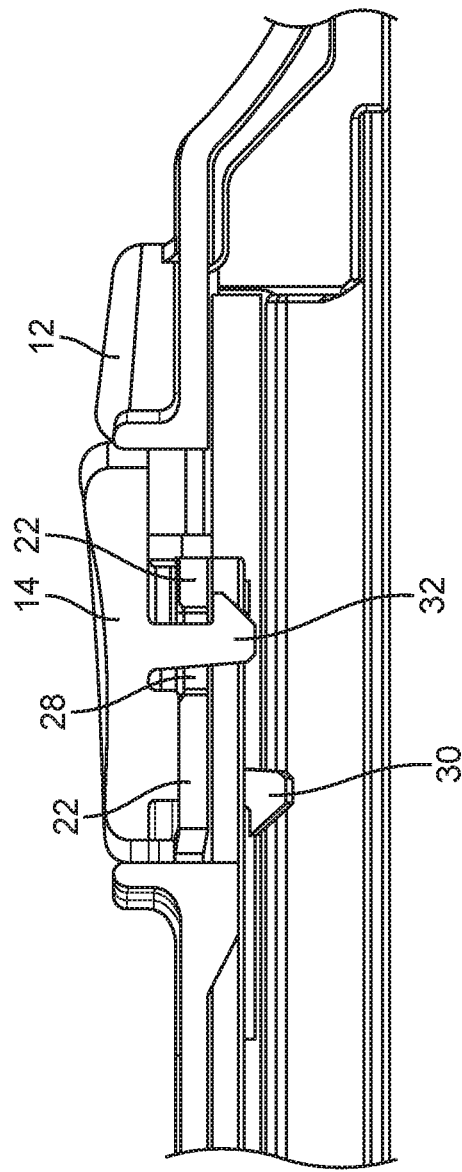

FIGS. 12A and 12B illustrate the mechanical coupling of the larger firing button 14 to the second lever 22. FIG. 12A is a detailed longitudinal cross-sectional view of the top half 16a of the biopsy device body 16 centered on the second opening 28 in the second lever 22. FIG. 12B depicts the larger firing button 14 mechanically coupled to the second lever 22 by first and second hooks 30, 32, which mate with first and second openings 26, 28, respectively. The first and second hooks 30, 32 form interference fits with portions of the body top half 16a set defined the first and second openings 26, 28. FIGS. 12A and 12B also show that the bottom surface 35 of the first lever 18 is higher than the bottom surface 38 of the second lever 22.

FIGS. 13A-C illustrate the interaction of the larger firing button 14 with the first and second levers 18, 22. FIGS. 13A and 13B show the first and second levers 18, 22 before and after installation of the larger firing button 14. FIG. 13C shows the larger firing button 14 in shadow after it has been mechanically coupled to the second lever 22. As shown in FIG. 13C, a proximal end 34 of the larger firing button 14 overlaps a distal end 36 of the first lever 18. This configuration of the larger firing button 14 and the first lever 18 allows actuation/depression of the larger firing button 14 to actuate the first lever 18 in addition to the second lever 22.

Figure 14A:
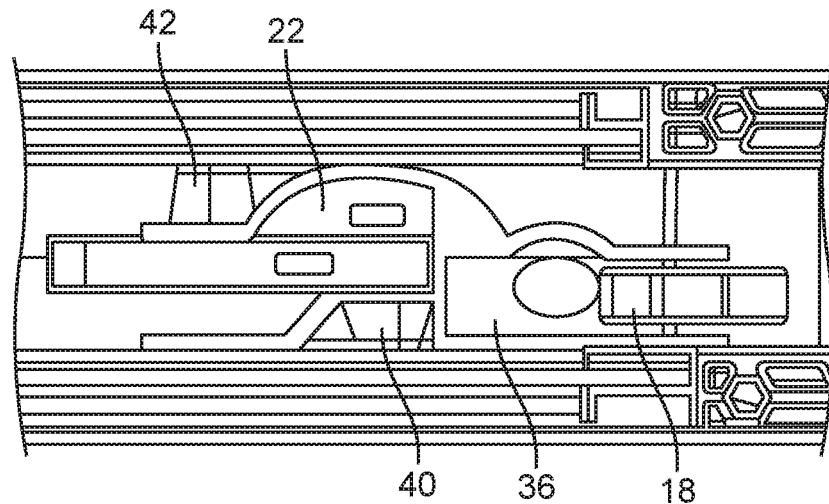
FIGS. 14A-B are detailed bottom views of the body depicted in FIG. 1A showing first and second levers, and first and second catches.
Figure 14B:
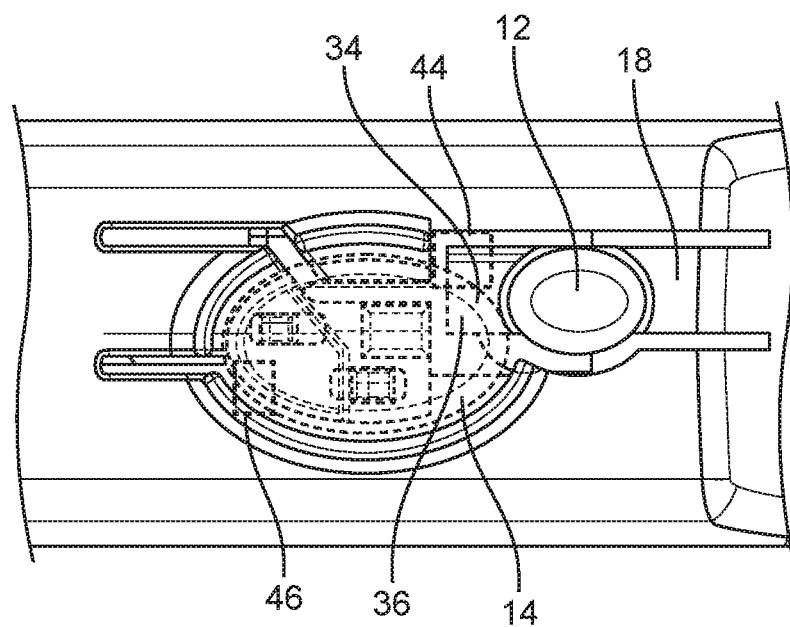

FIGS. 14A and 14B also illustrate the interaction of the larger firing button 14 with the first and second levers 18, 22. FIGS. 14A and 14B are bottom and top views of the portion of the body top half 16a including the first and second levers 18, 22. FIG. 14A also shows first and second catches 40, 42 defined on the body top half 16a, which are configured to retain inner needle latch 44 and outer cannula latch 46, to thereby arm the inner needle and the outer cannula (not shown), respectively. FIG. 14B shows the inner needle latch 44 and outer cannula latch 46 schematically as boxes. The inner needle latch 44 and outer cannula latch 46 are respectively attached to the inner needle and the outer cannula via needle carriage/hub 108 and cannula carriage/hub 102 (see FIG. 16). FIG. 14B also shows the larger firing button 14 installed and in shadow. FIG. 14B shows that, when the larger firing button is installed, the proximal end 34 of the larger firing button 14 overlaps the distal end 36 of the first lever 18.

Figure 15:
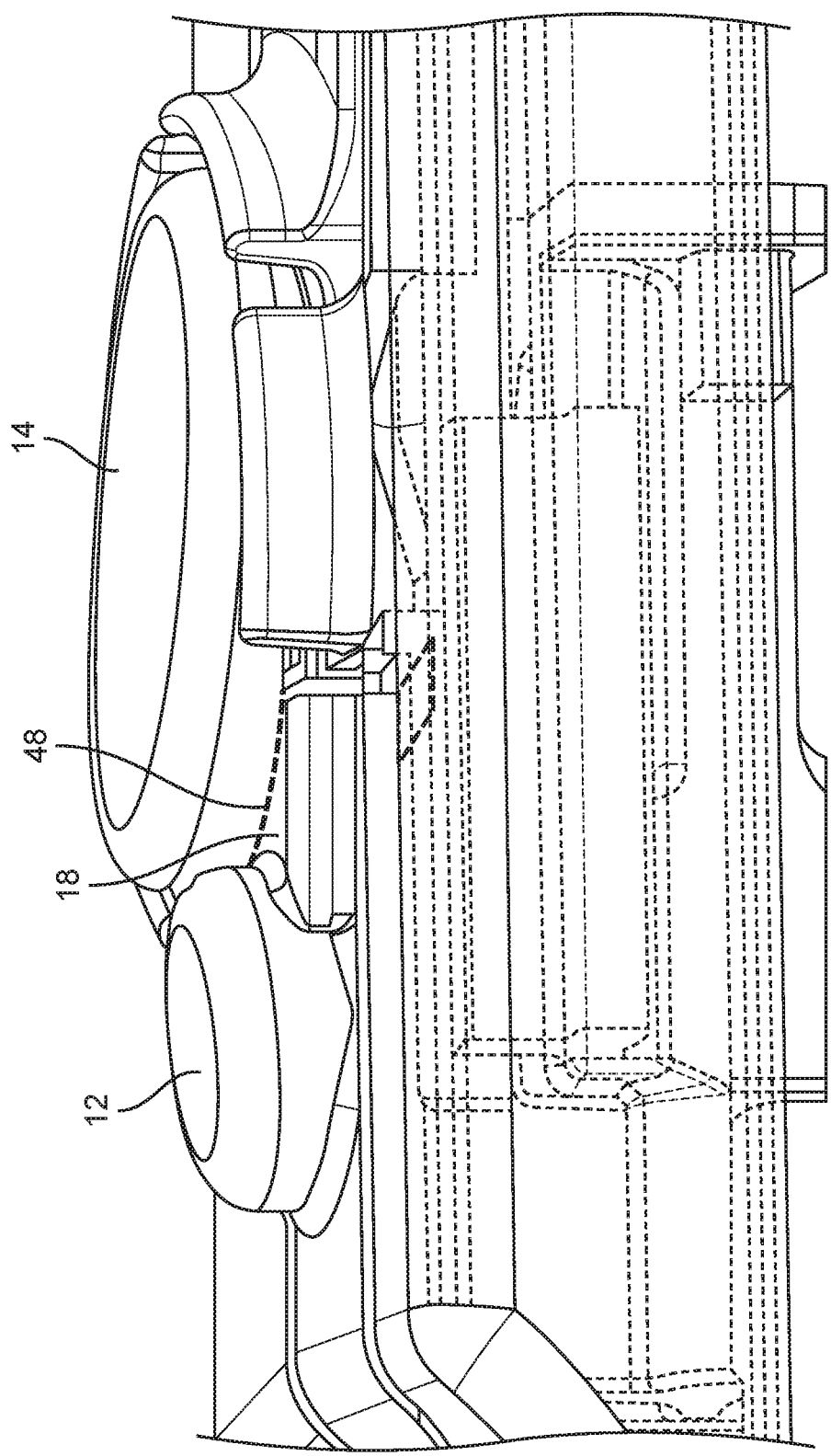
FIG. 15 is a detailed top view of the body depicted in FIG. 11A showing first and second levers, and large firing button, with a portion of the body shown in phantom for clarity.

FIG. 15 is a detailed perspective view of the portion of the biopsy device body 16 including the smaller and larger firing buttons 12, 14. FIG. 15 shows that when the larger firing button 14 is not actuated/depressed, there is a gap 48 between a bottom surface of the proximal end of the larger firing button 14 and the top contact surface of the distal end 36 of the first lever 18.

In use, the smaller firing button 12 is actuated/depressed to pivot the first lever 18, thereby releasing an inner needle latch 44. When the inner needle (not shown) is in an armed/non-fired position, releasing the inner needle latch 44 fires the inner needle (not shown). On the other hand, when the larger firing button 14 is actuated/depressed, both the first and second levers 18, 20 are pivoted. The proximal end 34 of the larger firing button 14 pivots the first lever 18 by acting on the distal end 36, thereby releasing the inner needle latch 44. The larger firing button 14 acts directly on the second lever 22 to pivot it, thereby releasing an outer cannula latch 46. Because the bottom surface 35 of the first lever 18 is higher than the bottom surface 38 of the second lever 22, actuating/depressing the larger firing button 14 first acts on first lever 18 and releases the inner needle latch 44, then acts on lever 22 and releases the outer cannula latch 46. When both the inner needle (not shown) and the outer cannula 104 are in their respective armed/non-fired positions, sequentially releasing the inner needle latch 44 and the outer cannula latch 46 sequentially fires the inner needle (not shown) and the outer cannula 104. When the inner needle (not shown) has been fired (e.g., by actuating/depressing the smaller firing button 12) and the outer cannula is in an armed/non-fired position, depressing the larger firing button 14 fires only the outer cannula 104.

Arming Mechanisms:

FIGS. 16 and 17A-C depict an embodiment of a biopsy device 10, and illustrate the arming mechanism for arming the outer cannula 104 and the inner needle (not shown). This arming mechanism is configured for use with the biopsy devices 10 depicted in FIGS. 1A, 1B and 4. Those biopsy devices 10 are armed by moving an arming button 110 or arming lever 60 (collectively "arming member") in a proximal direction. The embodiment depicted in FIGS. 16 and 17A-C may share some components or process steps with or be identical to other embodiments described above.

Figure 16:
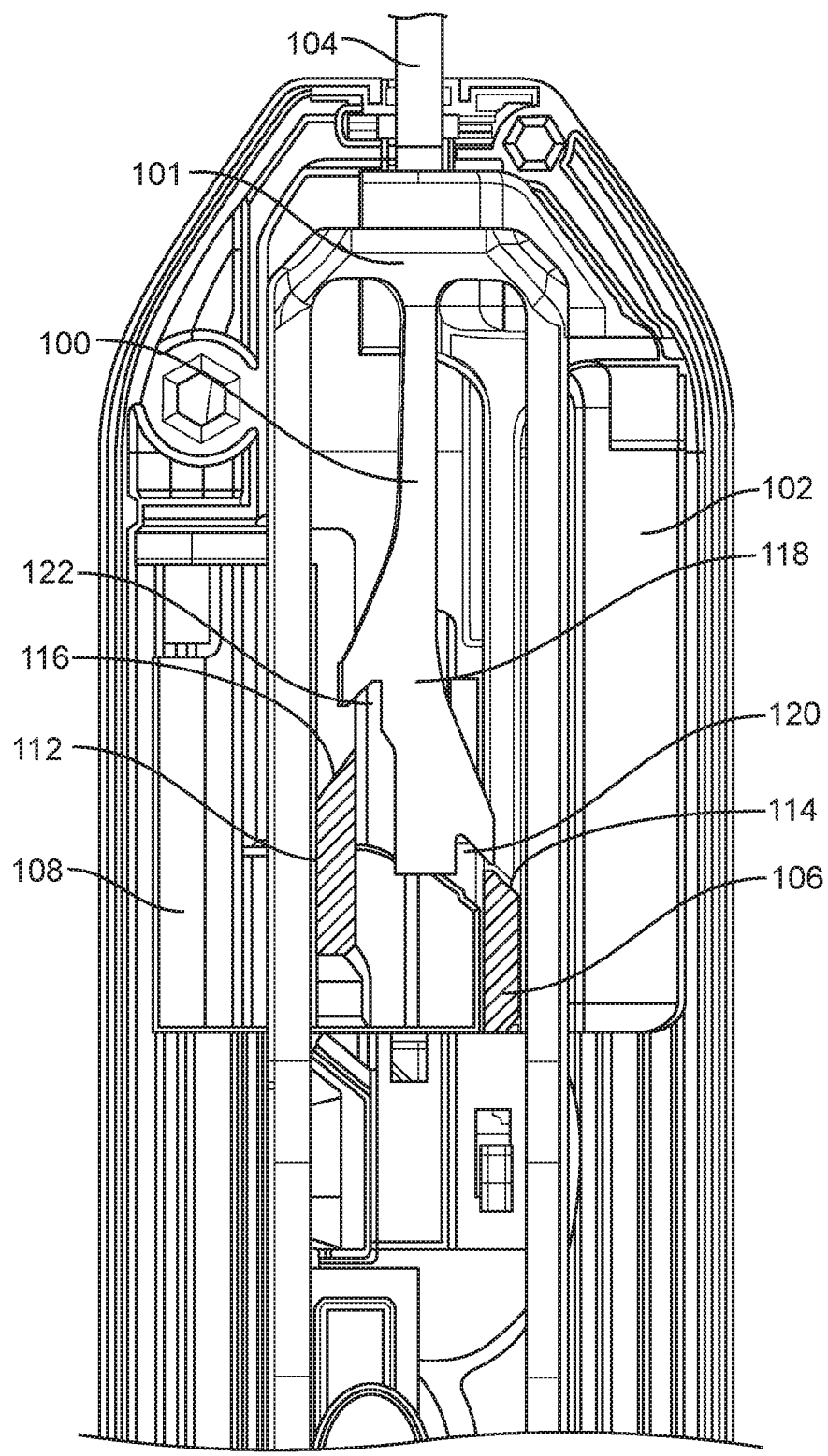

FIG. 16 illustrates an assembly for sequentially arming the outer cannula 104 and the inner needle (not shown). The assembly includes an arming body 101, having a resilient shaft 100, and which is operably coupled to an arming button 110 or arming lever 60 (see FIGS. 1A, 1B and 4) that is operable by a user. The assembly also includes a cannula carriage/hub 102 operably coupled to the outer cannula 104. The cannula carriage/hub 102 includes a cannula strike plate 106 disposed along a first edge of a travel path of the shaft 100 (adjacent a first recess 120 in the shaft 100, which is described below). Further the assembly includes a needle carriage/hub 108 operably coupled to the inner needle (not shown). The needle carriage/hub 108 includes a needle strike plate 112 disposed along a second opposite edge of the travel path of the shaft 100. When both the outer cannula 104 and inner needle are in their respective fired/unarmed positions, the needle strike plate 112 is disposed distal of the cannula strike plate 106.

The distal edge 114 of the cannula strike plate 106 forms a wedge/ramp with a high end adjacent the first edge of the travel path of the shaft 100 and the low end away from the first edge. The distal edge 116 of the needle strike plate 112 forms a wedge/ramp with a high end adjacent a second edge of the travel path of the shaft 100 (adjacent a second recess 122 in the shaft 100, which is described below) and the low end away from the second edge. As shown in FIG. 16, the distal edge 116 of the needle strike plate 112 is positioned more distally than the distal edge 114 of the cannula strike plate 106.

The proximal end 118 of the shaft 100 is enlarged forming first and second recesses 120, 122 (collectively a "catch") configured to receive the respective distal edges 114, 116 of the cannula strike plate 106 and the needle strike plate 112. The first recess 120, formed along the first edge of the travel path of the shaft 100 and configured to receive the distal edge 114 of the cannula strike plate 106, is disposed more proximally along the travel path of the shaft 100 than the second recess 122. The axial distance between the first and second recesses 120, 122 is greater than the axial distance between the distal edges 114, 116 of the cannula and needle strike plates 106, 112. Accordingly, as the shaft 100 and its proximal end 118 travel proximally along its travel path, the first recess 120 is configured to receive the distal edge 114 of the cannula strike plate 106 before the second recess 122 receives the distal edge 116 of the needle strike plate 112.

In use, when both the inner needle (not shown) and the outer cannula 104 are in their respective fired/unarmed positions, the user applies proximally directed force to the shaft 100 by actuating/depressing the arming button 110 or arming lever 60 (see FIGS. 1A, 1B and 4). The proximally directed force moves the shaft 100 proximally in the direction shown in FIG. 17A along the travel path for the shaft 100 using a compressive arming stroke. Each movement of the shaft 100 between opposite ends of the travel path and back is a "stroke." During a first stroke, the first recess 120, which is formed proximally on the proximal end 118 of the shaft 100, first encounters the distal edge 114 of the cannula strike plate 106. As shown in FIG. 17A, when the first recess 120 contacts the distal edge 114 of the cannula strike plate 106, the resistive force exerted by the wedge/ramp in distal edge 114 redirects the proximally directed force laterally, thereby pulling the proximal end 118 of the shaft 100 laterally toward the cannula strike plate 106 and away from the needle strike plate 112.

Figure 17C:
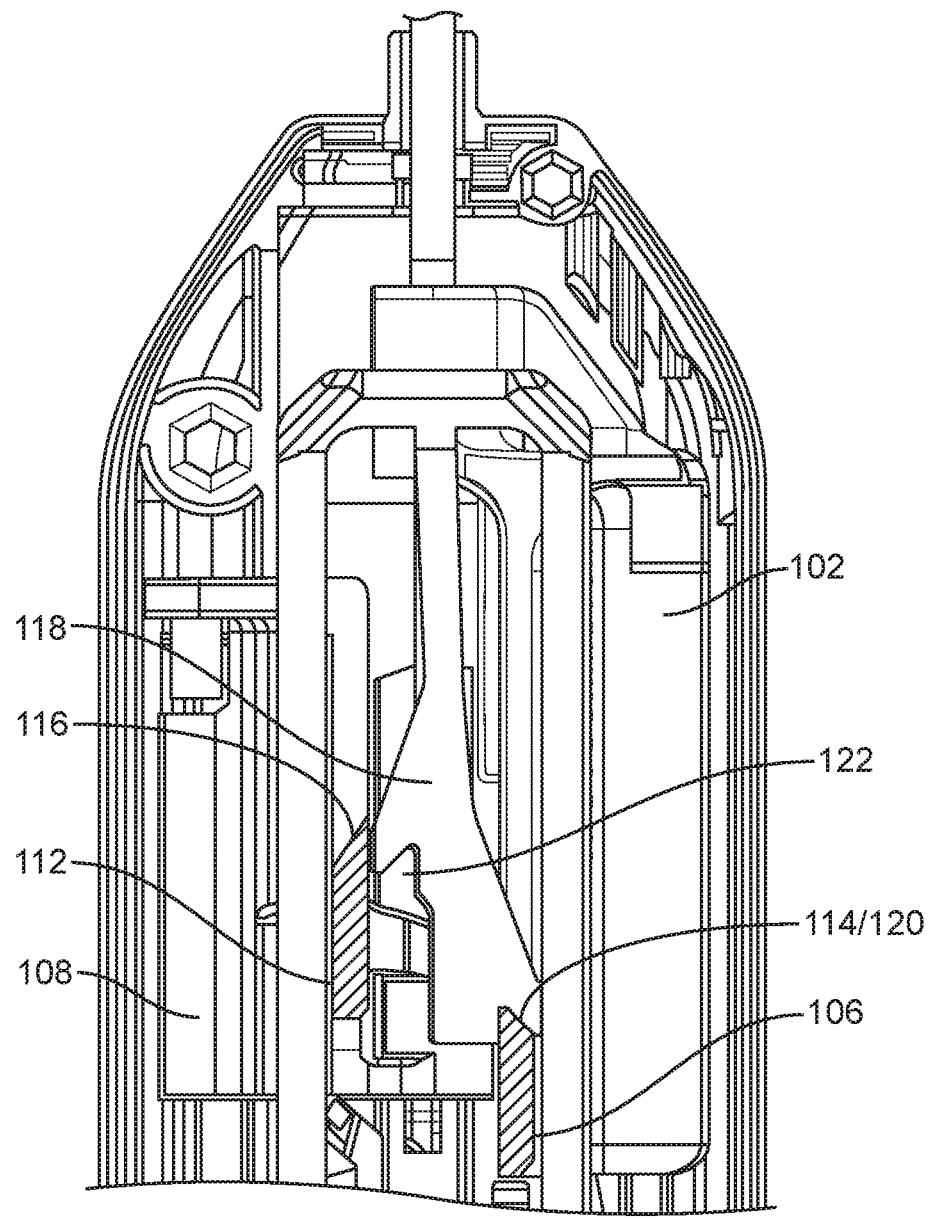

As shown in FIG. 17B, when the distal edge 114 of the cannula strike plate 106 is received in the first recess 120, the proximal end 118 of the shaft 100 is pulled laterally away from the needle strike plate 112. At this point, proximal movement of the cannula strike plate 106 and the cannula carriage/hub 102 continues as the spring force resisting same is overcome. As shown in FIG. 17C, the lateral movement of the proximal end 118 of the shaft 100 allows the shaft 100 and the cannula carriage/hub 102 attached thereto (via the cannula strike plate 106) to move proximally without the proximal end 118 of the shaft 100 engaging the needle strike plate 112. During the first stroke, a cannula latch (not shown) on the cannula carriage/hub 102 engages a first catch (not shown) and locks the cannula carriage/hub 102, and the outer cannula 104, in their armed position.

The user then releases the arming button 110 or arming lever 60 (see FIGS. 1A, 1B and 4), which is reset distally by an arming button biasing spring (not shown, but see FIG. 26 for a similar spring) disposed between the arming button 110 and the proximal end of the biopsy device body 16. Next the user again applies proximally directed force to the arming button 110 or arming lever 60 (see FIGS. 1A, 1B and 4) to initiate a second stroke. With the cannula carriage/hub 102 locked in its armed position, the proximal end 118 of the shaft 100 engages the distal edge 116 of the needle strike plate 112 during the second stroke to arm the inner needle (not shown) as described above for the outer cannula 104.

While the cannula and needle strike plates 106, 112 depicted in FIGS. 16 and 17A-C form wedges/ramps, the cannula and needle strike plates 106, 112 can take any form. While the cannula and needle strike plates 106, 112 depicted in FIGS. 16 and 17A-C are offset from the middle of the longitudinal axis along the travel path for the shaft 100 (while being longitudinally aligned with the first and second recesses 120,122 when is shaft 100 is not deflected), the cannula and needle strike plates 106, 112 can be disposed along the middle of the longitudinal axis. The form and location of the cannula and needle strike plates 106, 112 can vary as long as they are configured to cooperate with respective first and second recesses 120, 122 such that when the first recess 120 engages the cannula strike plate 106, the proximal end 118 of the shaft 100 is moved so that the second recess 122 does not engage the needle strike plate 112 during that stroke.

Figure 18:
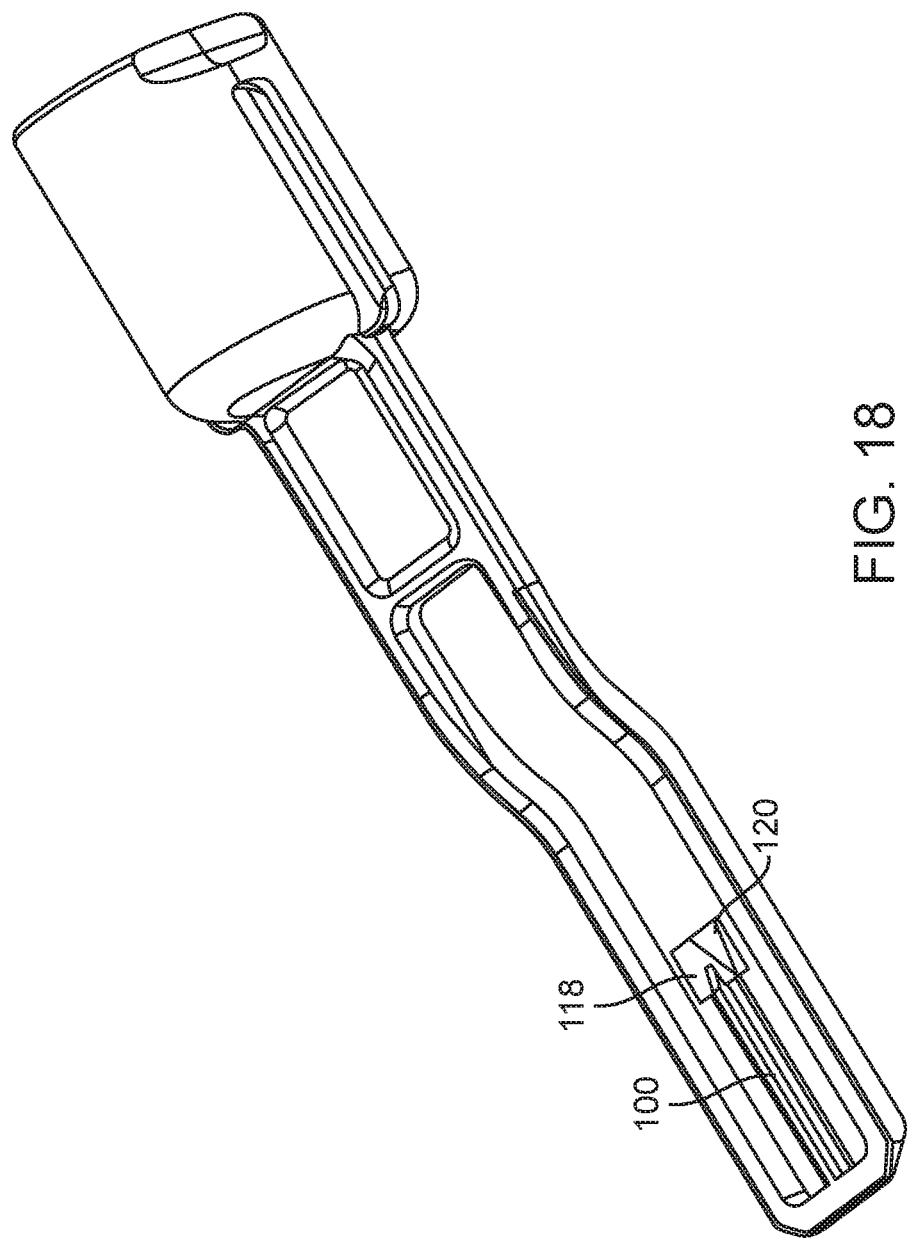
FIGS. 18-20 are perspective views of an arming button and arming member of a spring loaded core biopsy device according to two other embodiments.
Figure 19:
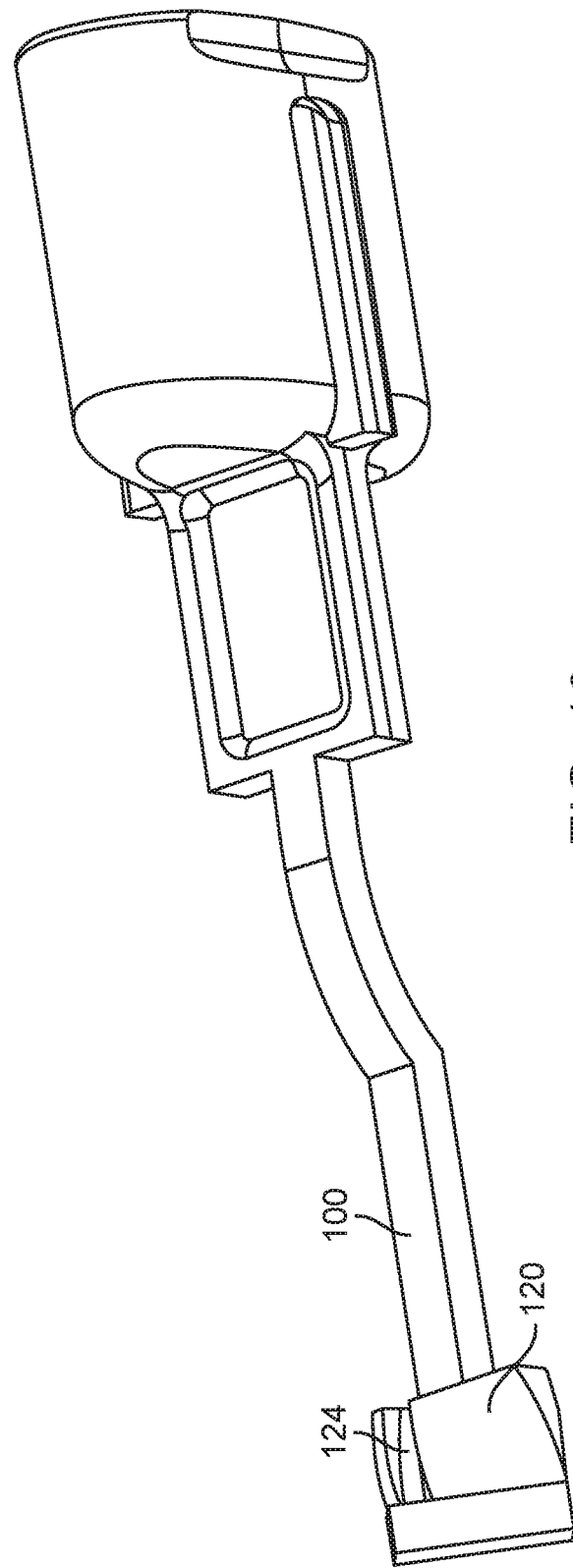
Figure 20:
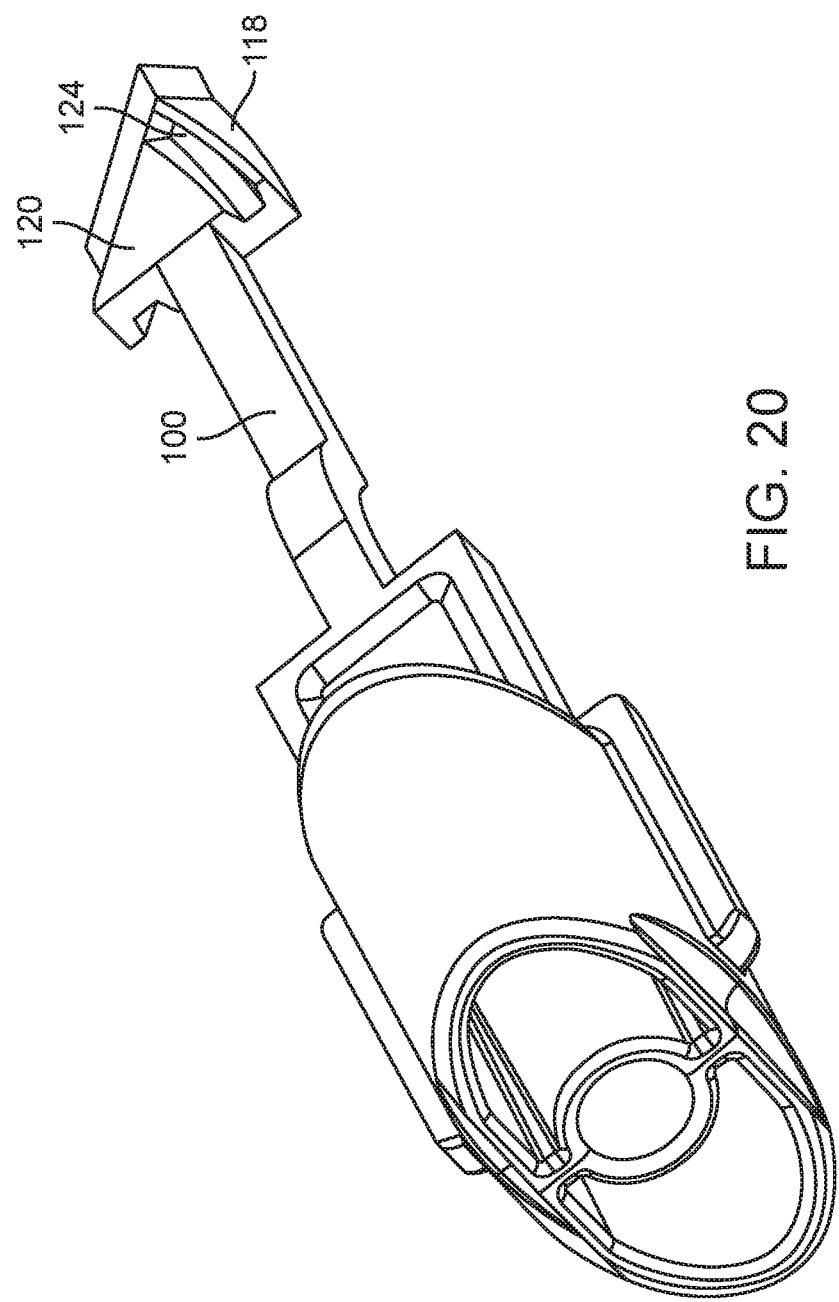

FIGS. 18-20 depict two similar embodiments of shafts 100 having different proximal ends 118 from the embodiment depicted in FIGS. 16 and 17A-C. In the embodiment shown in FIG. 18, the first and second recesses 120, 122 each form a wedge/ramped surface that is configured to twist the proximal end 118 of the shaft 100 about it longitudinal axis when urged axially against the respective distal edges 114, 116. In the embodiment shown in FIGS. 19 and 20, the first and second recesses 120, 122 each form a helically twisting two-dimensional surface having a helically twisting trough/guide 124 that is configured to twist the proximal end 118 of the shaft 100 about its longitudinal axis when urged proximally against the respective distal edges 114, 116. For use with the embodiments depicted in FIGS. 18-20, the distal edges 114, 116 of the cannula and needle strike plates 106, 112 (not shown) can each form a wedge/ramped surface, or other surface configured to interact the respective first and second recesses 120, 122, as described above. For instance, for use with the embodiment depicted in FIGS. 18-20, the distal edges 114, 116 of the cannula and needle strike plates 106, 112 (not shown) can each form a point configured to enter into and travel along the troughs/guides 124 of the respective first and second recesses 120, 122.

For use of the embodiment shown in FIG. 18, when the distal edge 114 of the more distally disposed cannula strike plate 106 contacts the proximally moving proximal end 118 of the shaft 100, the helically twisting two-dimensional surface and the helically twisting trough/guide 124 of the first recess 120 interacts with the distal edge 114 to twist the proximal end 118 of the shaft 100. As a result of this twisting motion, the proximal end 118 of the shaft 100 does not engage the distal edge 116 of the needle strike plate 112 during a first stroke when both the inner needle (not shown) and the outer cannula 104 are in their respective fired/unarmed positions. On a second stroke, the cannula carriage/hub 102 is locked in its armed position, the proximal end 118 of the shaft 10 bypasses the cannula strike plate 106, and the proximal end 118 of the shaft 100 contacts the distal edge 116 of the needle strike plate 112 to arm the inner needle (not shown).

For use of the embodiment shown in FIGS. 19 and 20, when the distal edge 114 of the more distally disposed cannula strike plate 106 contacts the proximally moving proximal end 118 of the shaft 100, the wedge/ramped surface of the first recess 120 interacts with the distal edge 114 to twist the proximal end 118 of the shaft 100. As a result of this twisting motion, the proximal end 118 of the shaft 100 does not engage the distal edge 116 of the needle strike plate 112 during a first stroke with both the inner needle (not shown) and the outer cannula 104 are in their respective fired/unarmed positions. On a second stroke, the cannula carriage/hub 102 is locked in its armed position, the proximal end 118 of the shaft 10 bypasses the cannula strike plate 106, and the proximal end 118 of the shaft 100 contacts the distal edge 116 of the needle strike plate 112 to arm the inner needle (not shown).

FIGS. 21A-25B depict an arming mechanism according to another embodiment that is configured for use with the biopsy device 10 depicted in FIGS. 2A, 2B and 5. Those biopsy devices 10 are armed by relative motion between an arming button (or "arming member") 110 and a biopsy device body 16. For instance, the devices 10 can be armed by (1) moving the arming button 110 in a distal direction while keeping the biopsy device body 16 stationary; (2) moving the biopsy device body 16 in a proximal direction while keeping the arming button 110 stationary; or (3) moving the arming button 110 in a distal direction while moving the biopsy device body 16 in a proximal direction. The embodiment depicted in FIGS. 21A-25B may share some components or process steps with or be identical to other embodiments described above.

Figure 21A:
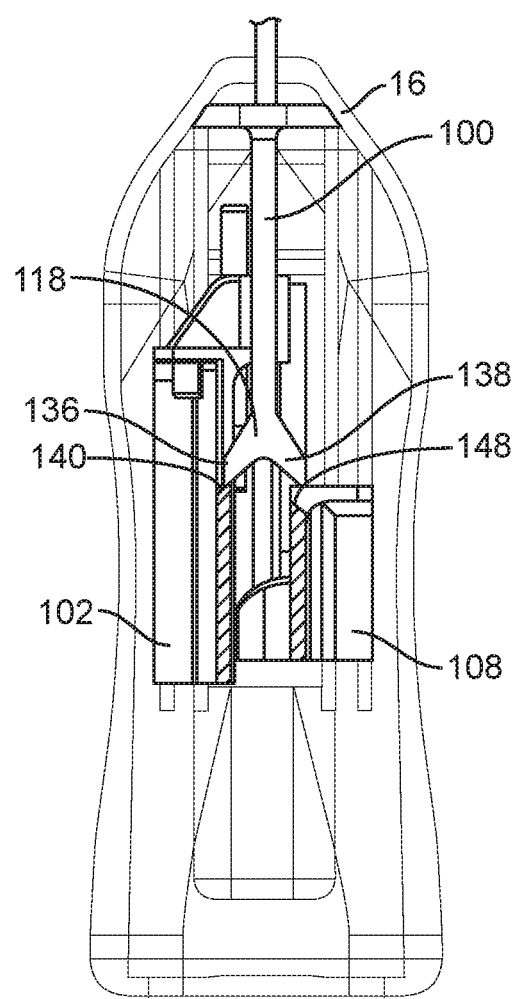
FIGS. 21A-25B are top longitudinal cross-sectional views of the spring loaded core biopsy device depicted in FIG. 2 at various steps of a first and a second arming stroke and at various levels (figures A vs. figures B).
Figure 21B:
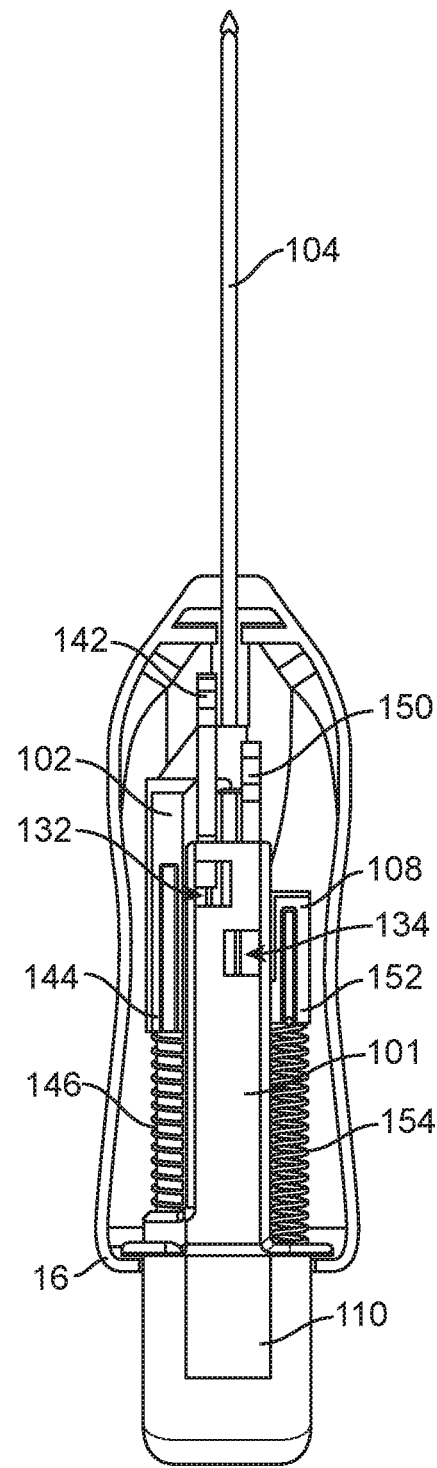
Figure 22A:
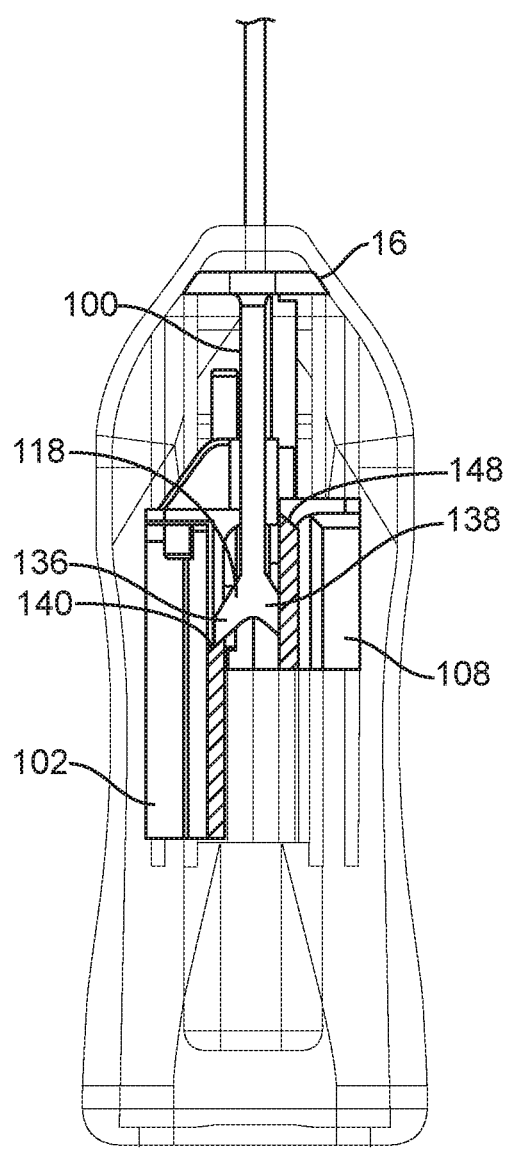
Figure 22B:
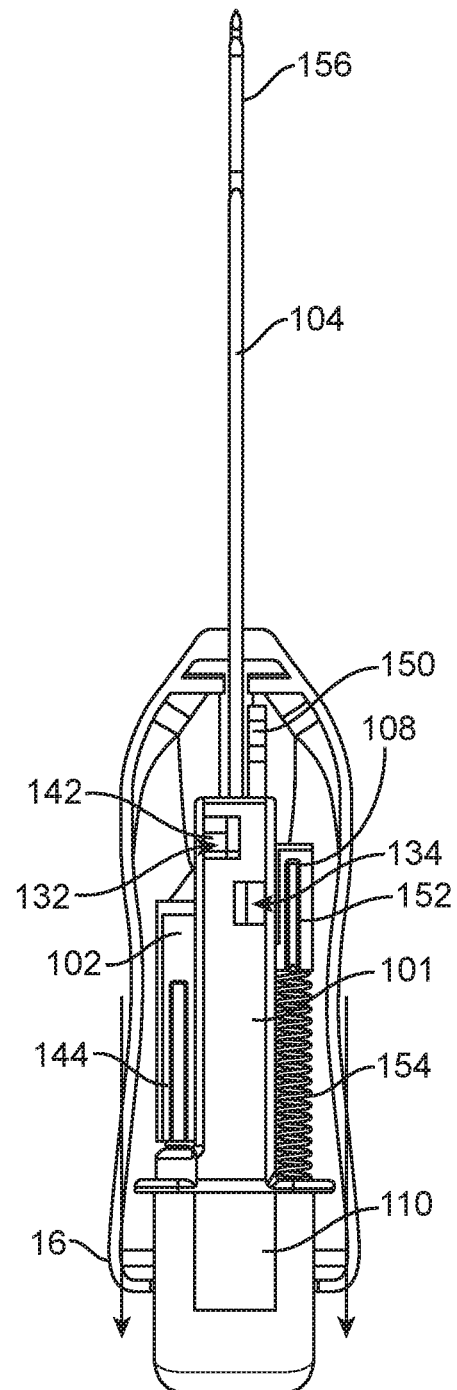

FIG. 21B illustrates an assembly for sequentially arming the outer cannula 104 and the inner needle (not shown). The assembly includes an arming body 101 including, or operably coupled to, an arming button 110 that is operable by a user. The arming body 101 includes cannula and needle notches 132, 134, which are configured to retain cannula and needle carriages/hubs 102, 108 in their respective proximal/armed positions. The assembly also includes a resilient shaft 100 extending proximally from the distal end of the biopsy device body 16 (see FIG. 21A). The proximal end 118 of the resilient shaft 100 takes the form of a "Y" having first and second proximally and orthogonally extending arms 136, 138, which are configured to interact with the cannula and needle carriages/hubs 102, 108. The arming body 101 (attached to the arming button 110) and the resilient shaft 100 (attached to the biopsy device body 16) are located and different depths in the biopsy device 10, such that the arming body 101 and the resilient shaft 100 can partially overlap each other during the arming process. The cannula and needle carriage/hubs 102, 108 span the depths at which the arming body 101 and the resilient shaft 100 are disposed, and therefore can interact with each of the arming body 101 and the resilient shaft 100.

The cannula carriage/hub 102 is operably coupled to the outer cannula 104. The cannula carriage/hub 102 includes a cannula strike surface 140 disposed along a first edge of a travel path of the shaft 100 and the depth level of the resilient shaft 100 (see FIG. 21A). At the depth level of the arming body 101, the cannula carriage/hub 102 includes a cannula catch 142 configured to operatively couple to the arming body 101 via the cannula notch 132. The cannula carriage/hub 102 also includes a cannula spring holder 144 configured to compress a cannula firing (or "biasing") spring 146 against a proximal end of the biopsy device body 16.

The needle carriage/hub 108 is operably coupled to the inner needle (not shown). The needle carriage/hub 108 includes a needle strike surface 148 disposed along a second opposite edge of the travel path of the shaft 100 and the depth level of the resilient shaft 100 (see FIG. 21A). At the depth level of the arming body 101, the needle carriage/hub 108 includes a needle catch 150 configured to operatively couple to the arming body 101 via the needle notch 134. The needle carriage/hub 108 also includes a needle spring holder 152 configured to compress a needle firing (or "biasing") spring 154 against a proximal end of the biopsy device body 16.

When both the outer cannula 104 and inner needle are in their respective fired/unarmed positions, the cannula strike surface 140 is disposed distal of the needle strike surface 148. The distal edge of the cannula strike surface 140 forms a wedge/ramp with a high end adjacent the first edge of the travel path of the shaft 100 and the low end away from the first edge. The distal edge of the needle strike surface 148 forms a wedge/ramp with a high end adjacent a second edge of the travel path of the shaft 100 and the low end away from the second edge. As shown in FIG. 21A, the distal edge of the needle strike surface 148 is positioned more proximally than the distal edge of the cannula strike surface 140.

The cannula strike surface 140 along the first edge of the travel path of the shaft 100 is configured to cooperate with the first arm 136 of the resilient shaft 100. The needle strike surface 148 along the second edge of the travel path of the shaft 100 is configured to cooperate with the second arm 138 of the resilient shaft 100. The distal edge of the needle strike surface 148 is positioned more proximally than the distal edge of the cannula strike surface 140. Accordingly, with both the outer cannula 104 and inner needle are in their respective fired/unarmed positions, as the shaft 100 and its proximal end 118 travel proximally along its travel path, the first arm 136 interacts with the cannula strike surface 140 before the second arm 138 interacts with the needle strike surface 148.

In use, when both the inner needle 156 and the outer cannula 104 are in their respective fired/unarmed positions, the user applies proximally directed force to the shaft 100 by actuating/depressing the arming button 110 (see the transition from FIGS. 21A and 21B to FIGS. 22A and 22B), or depressing the biopsy device body 16 with the arming button 1/10 secured against a stable surface. Both these motions move the biopsy device body 16, and the resilient shaft 100 attached thereto, proximally relative to the arming button 110, using a compressive arming stroke. The proximally directed force moves the shaft 100 proximally in the direction shown in FIG. 21A along the travel path for the shaft 100. Each movement of the shaft 100 between opposite ends of the travel path and back is a "stroke."

During a first stroke, the cannula strike surface 140, which is positioned distally relative to the needle strike surface 148, first encounters the first arm 136 at the proximal end 118 of the resilient arm 100. When the first arm 136 contacts the distal edge of the cannula strike surface 140, the resistive force exerted by the wedge/ramp in distal edge 114 redirects the proximally directed force laterally, thereby pulling the proximal end 118 of the shaft 100 laterally toward the cannula strike surface 140 and away from the needle strike surface 148, such that the second arm 138 does not interact with the needle strike surface 148 on the first stroke.

As the stroke continues, proximal movement of the cannula strike surface 140 and the cannula carriage/hub 102 compresses the cannula firing spring 146. In the middle of the first stroke, the cannula catch 142 is disposed in the cannula notch 132 in the arming body 101, and locks the cannula carriage/hub 102 and the outer cannula 104, in their armed position (see FIG. 23B).

Figure 23A:
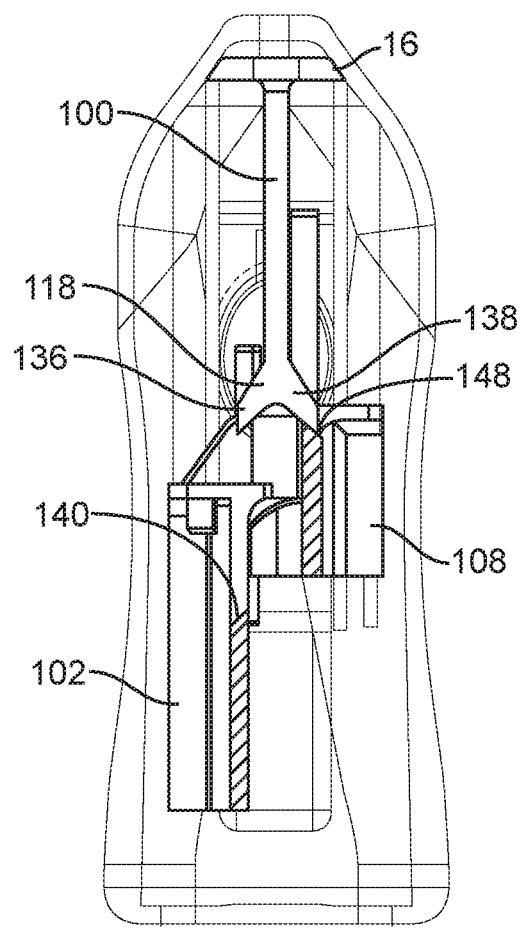
Figure 23B:
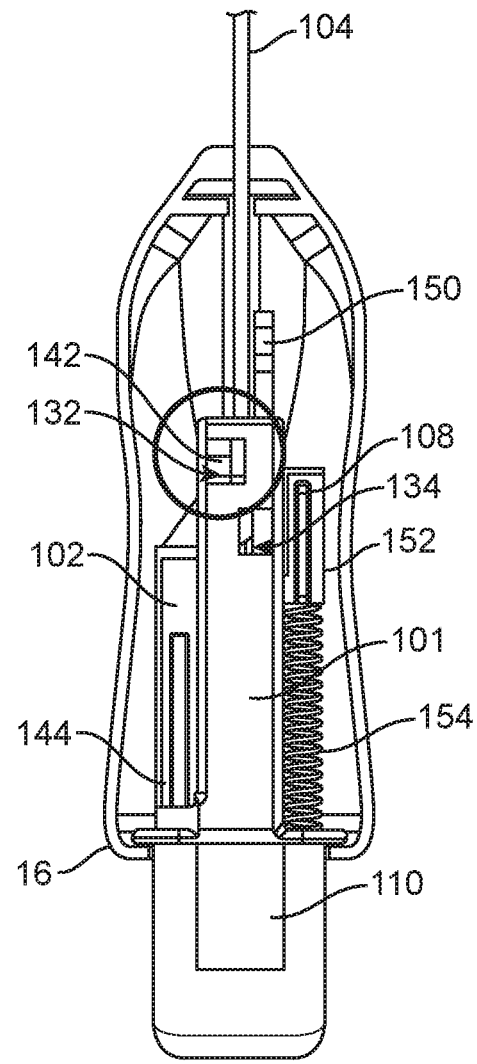
Figure 24A:
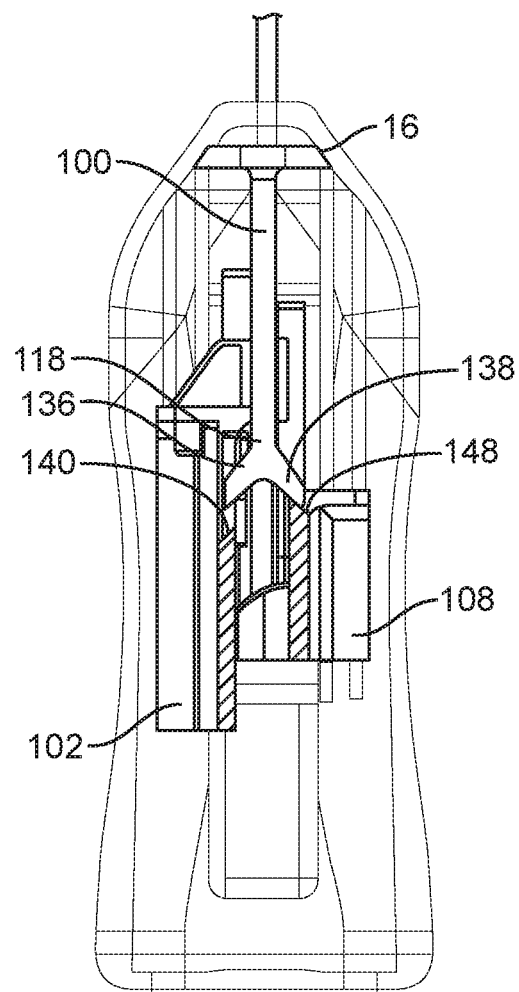
Figure 24B:
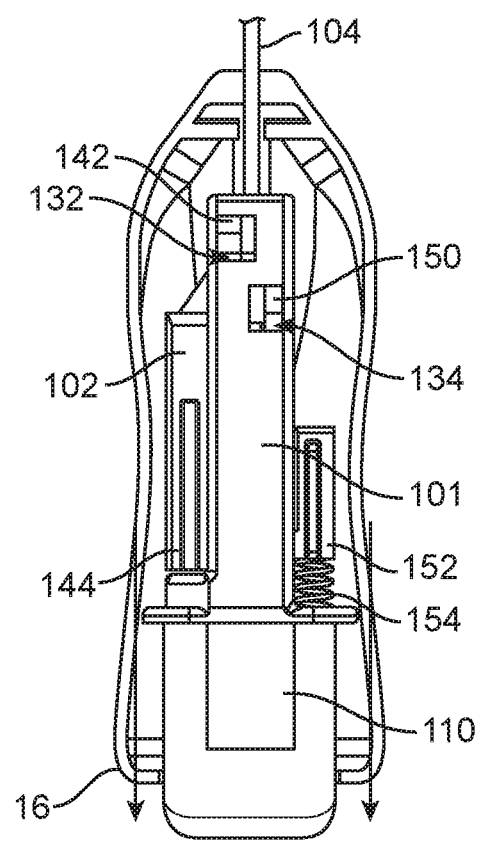
Figure 25A:
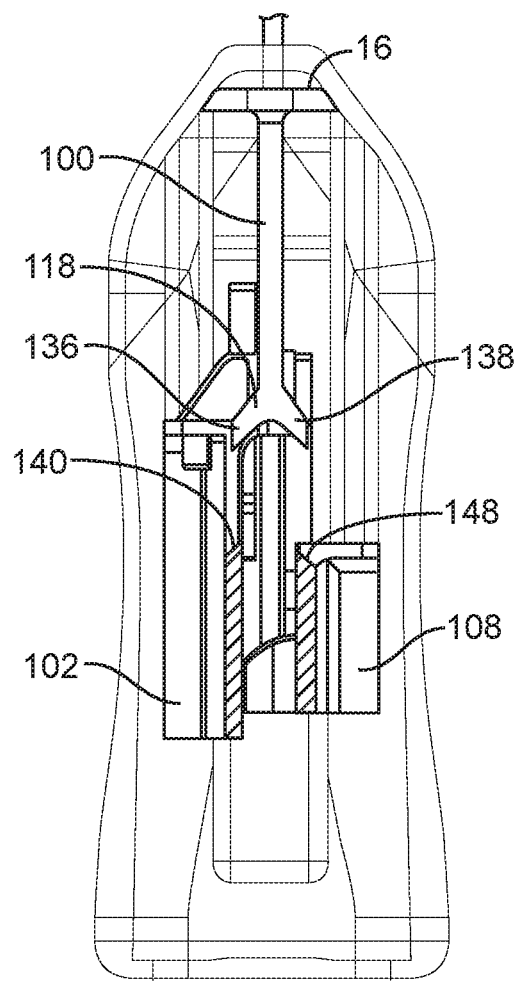
Figure 25B:
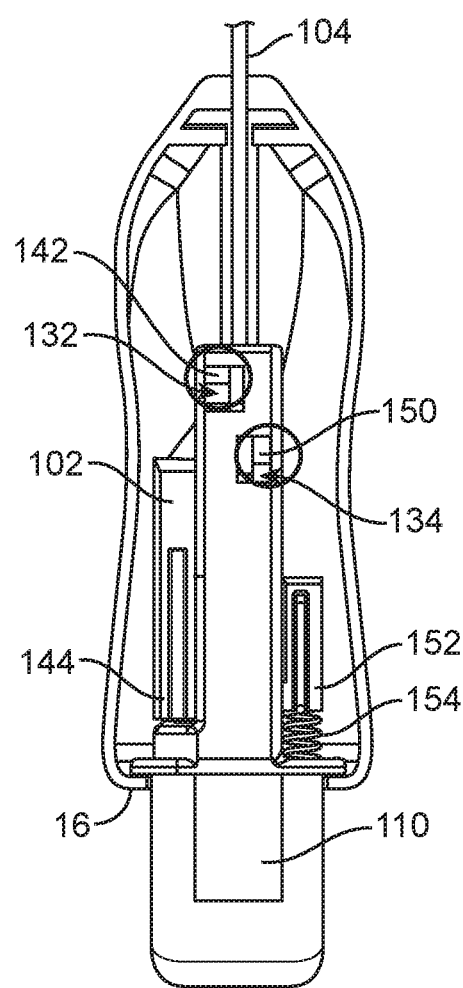

The user then releases the arming button 110 or biopsy device body 16, which is reset proximally (arming button 110) or distally (biopsy device body 16) by an arming button biasing spring (not shown, but see FIG. 26 for a similar spring) (see FIGS. 23A and 23B). Next the user again applies distally directed force to the arming button 110 (relative to the biopsy device body) or proximally directed force to the biopsy device body 16 (relative to the arming button 110) (see FIGS. 24A and 24B) to initiate a second stroke. With the cannula carriage/hub 102 locked in its armed position, the proximal end 118 of the shaft 100 engages the needle strike surface 148 during the second stroke to arm the inner needle 156 as described above for the outer cannula 104. As the second stroke continues, proximal movement of the needle strike surface 148 and the needle carriage/hub 108 compresses the needle firing spring 154. During the second stroke, the needle catch 150 is disposed in the needle notch 134 in the arming body 101 and locks the needle carriage/hub 108, and the inner needle 156, in their armed position (see FIG. 24B). The user then releases the arming button 110 or biopsy device body 16, which is reset proximally by a spring (see FIGS. 25A and 25B).

While the cannula and needle strike surfaces 140, 148 depicted in FIGS. 21A-25B form wedges/ramps, the cannula and needle strike surfaces 140, 148 can take any form, as described above. While the cannula and needle strike surfaces 140, 148 depicted in FIGS. 21A-25B are offset from the middle of the longitudinal axis of the shaft 100 (while being longitudinally aligned with the first and second arms 136,138 when is shaft 100 is not deflected), the cannula and needle strike surfaces 140, 148 can be disposed along the middle of the longitudinal axis. The form and location of the cannula and needle strike surfaces 140, 148 can vary as long as they are configured to cooperate with respective first and second arms 136, 138 such that when the first arm 136 engages the cannula strike surface 140, the proximal end 118 of the shaft 100 is moved so that the second arm 138 does not engage the needle strike surface 148 during that stroke. Further, the form and location of the proximal end 118 of the resilient shaft 100 can vary as long as it includes features (e.g., first and second arms 136, 138) configured to cooperate with respective cannula and needle strike surfaces 140, 148, as described above. For instance, the proximal end 118 of the resilient shaft 100 may be similar to the proximal end 118 depicted in FIG. 16.

Figure 26:
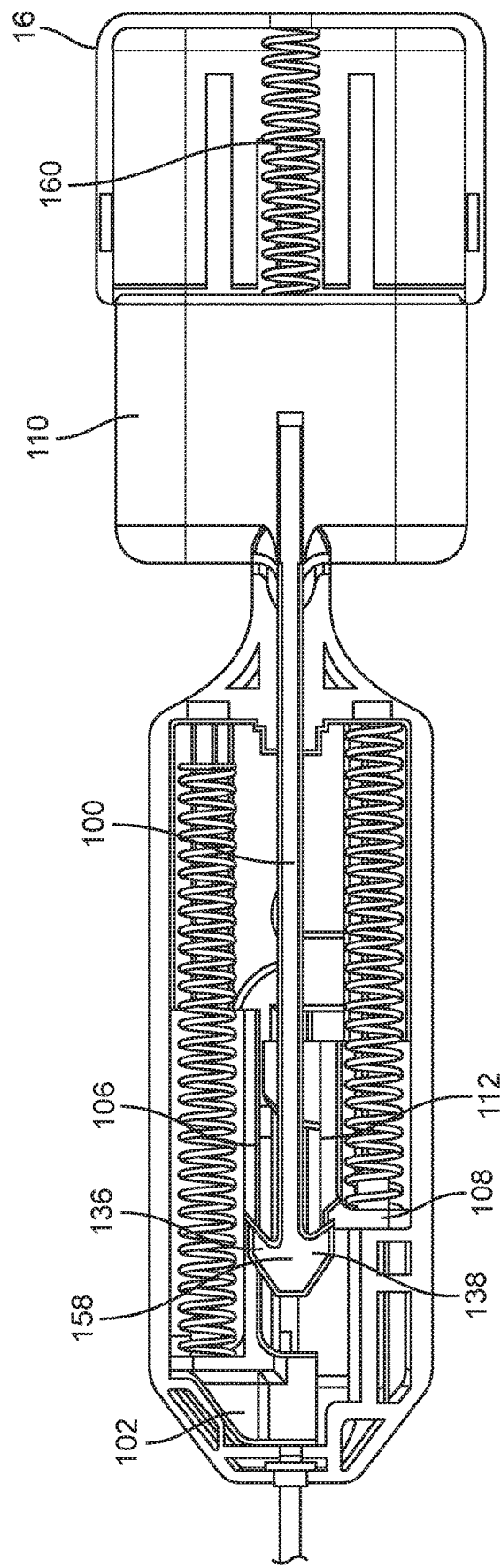
FIG. 26 is a top longitudinal cross-sectional view of an embodiment of a spring loaded core biopsy device according to another embodiment.

FIG. 26 depicts another embodiment of a biopsy device 10 (similar to one depicted in FIG. 1A) including an arming mechanism having a resilient shaft 100 that forms first and second arms 136, 138 at a distal end 158 thereof. The embodiment depicted in FIG. 26 functions similarly to the embodiments depicted in FIGS. 16, 17A-C and 21A-25A. The embodiment depicted in FIG. 26 shows an arming button biasing spring 160 disposed between the arming button 110 and the proximal end of the biopsy device body 16, and configured to return the button between arming strokes.

Removing Tissue from Biopsy Device:

Spring loaded core biopsy devices 10 are used to remove a sample of tissue from the patient for pathology (e.g., to determine whether cancerous cells are present). Typical spring loaded core devices 10 have a needle 202 with an aperture 206 (e.g., a slot) cut into it, and the needle 202 is disposed coaxially within a cutting cannula 204 having a sharpened distal edge 208. During a biopsy, the tissue prolapsed into the aperture 206 is severed by the cannula 204 as the cannula 204 translates over the aperture 206, forming a core of excised tissue 210. The cannula 204 is then retracted, exposing the excised tissue 210 contained in the aperture 206. The tissue is then removed from the aperture 206 and placed in fixative and analyzed.

There are several known methods for removing the excised tissue 210 from the aperture 206, including scraping the needle against an edge or the interior of a collection container, picking up with forceps and depositing into a collection container, shaking or tapping of the needle to dislodge the excised tissue 210 into a collection container, or wiping the tissue specimen onto a piece of gauze and depositing into a collection container. Known methods for removing the excised tissue 210 from the aperture 206 can be time-consuming, but the excised tissue 210 must be removed from the aperture 206 before additional tissue can be biopsied. Further, all of the above-described known methods risk dropping or otherwise contaminating the excised tissue core 210 during transfer into the collection container.

Figure 27:
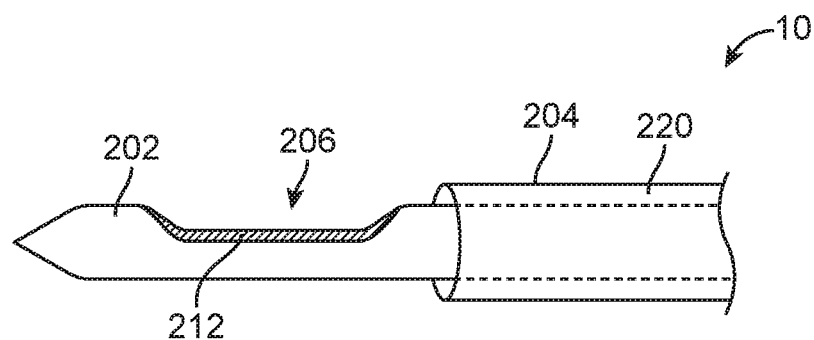
FIG. 27 is a side longitudinal cross-sectional view of the distal ends of a needle and a cannula of a spring loaded core biopsy device according to one embodiment.

FIGS. 27-31 illustrate various embodiments for removing excised tissue 210 from the aperture 206 of a spring loaded core device 10. FIG. 27 depicts an embodiment of a spring loaded core device 10 in which the aperture 206 in the needle 202 is coated with a lubricious material 212 that resists adherence of the tissue to the aperture. Fatty tissue is the typical tissue that adheres to the aperture 206 in metallic needles 202. Accordingly, the lubricious material 212 coating may be oleophobic, hydrophobic, or both.

Figure 28:
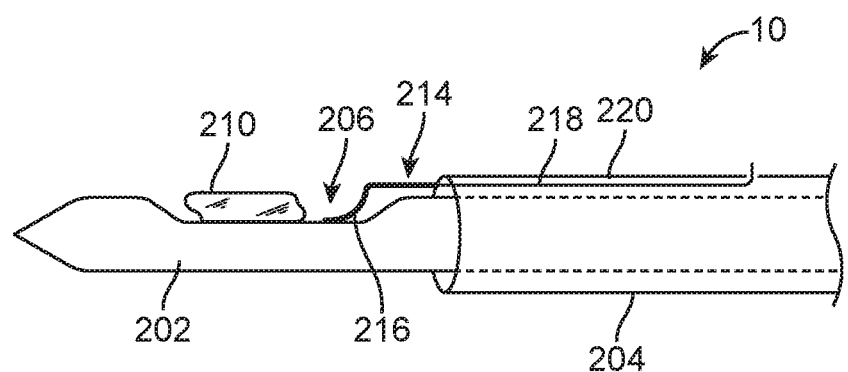
FIGS. 28 and 29 are side longitudinal cross-sectional views of the distal ends of a needle and a cannula of a spring loaded core biopsy device according to another embodiment.
Figure 29:
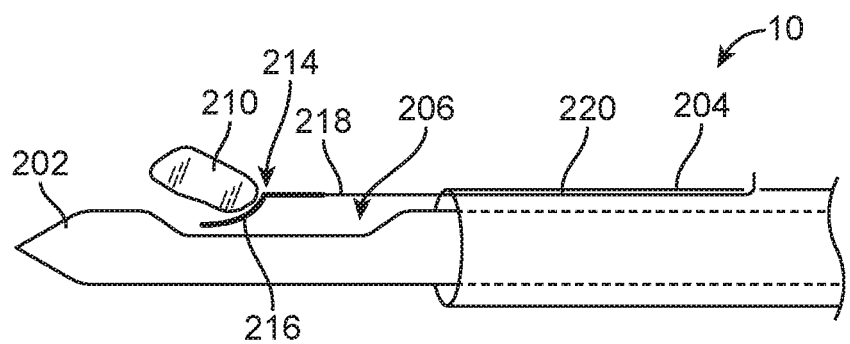

FIGS. 28 and 29 depict another embodiment in which the spring loaded core device 10 includes a pushing device 214 configured to remove the excised tissue core 210 from the aperture 206 by mechanically pushing and/or scraping. The pushing device 214 includes a scoop, spatula, or other shaped body 216 disposed in the aperture 206 and having a proximal end coupled to an elongate body 218 (e.g., a thin wire), which runs along the length of the spring loaded core device 10 in an annular space 220 between the needle 202 and the cannula 204. As shown in FIG. 29, the scoop/spatula/shaped body 216 can be advanced distally using the elongate body 218 to dislodge/eject the excised tissue core 210 from the aperture 206. After dislodging or ejecting the excised tissue core 210, the scoop/spatula/shaped body 216 can be retracted into the annular space 220. Alternatively, the scoop/spatula/shaped body 216 can sit (substantially flush) against the proximal end of the aperture 206 when not in use.

Figure 30:
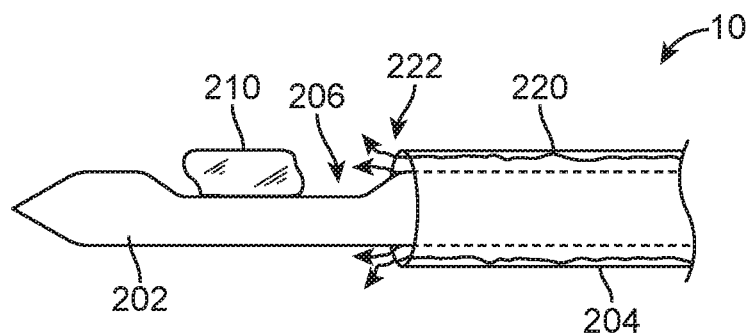
FIG. 30 is a side longitudinal cross-sectional view of the distal ends of a needle and a cannula of a spring loaded core biopsy device according to another embodiment.
Figure 31:
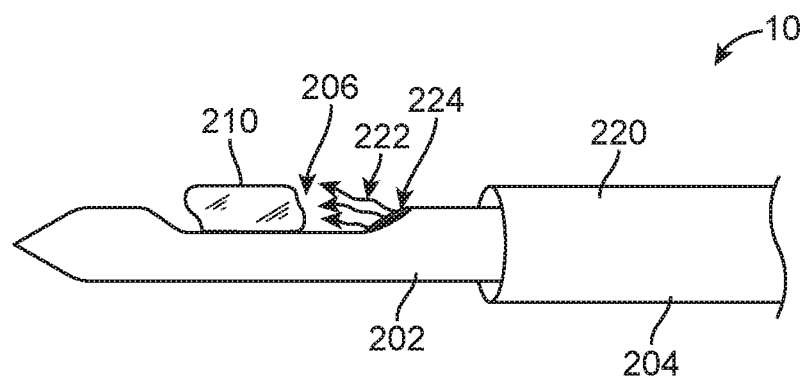
FIG. 31 is side longitudinal cross-sectional view of the distal ends of a needle and a cannula of a spring loaded core biopsy device according to still another embodiment.

FIGS. 30 and 31 depict two related embodiments of spring loaded core devices 10 that use a flushing fluid 222, such as saline, to flush the excised tissue core 210 from the aperture 206 and into a collection vial (not shown). In the embodiment depicted in FIG. 30, the flushing fluid 222 is pushed distally through the spring loaded core device 10 in the annular space 220 between the needle 202 and the cannula 204. A port (not shown) on the spring loaded core device 10 can be attached to a syringe (not shown) filled with the flushing fluid 222 to provide the flushing fluid 222 under pressure. In the embodiment depicted in FIG. 31, the flushing fluid 222 is pushed distally through the spring loaded core device 10 in the lumen 224 of a hollow needle 202. This embodiment provides a more direct flow of the flushing fluid 222 into the aperture 206 to flush the excised tissue core 210 therefrom.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A method for performing a biopsy using a hand-held biopsy device, the method comprising:
with a single hand, manually depressing an arming member of the hand-held biopsy device toward a proximal portion of a housing of the hand-held biopsy device and away from a distal portion of the housing of the hand-held biopsy device a first time to thereby compress the arming member and simultaneously move a cannula hub positioned in the distal portion of the housing from a cannula hub extended position to a cannula hub armed position,
wherein, throughout a full range of movement of the arming member and a full range of movement of the cannula hub, a position of the arming member is proximal to a position of the cannula hub.

2. The method of claim 1, wherein manually depressing the arming member comprises depressing a distally facing arming actuation surface of the arming member proximally relative to the distal portion of the housing.

3. The method of claim 2, wherein manually depressing the arming member comprises:
placing a proximal end surface of the housing in a palm of the single hand,
placing one or more fingers of the single hand onto the arming actuation surface, and
squeezing the arming member toward the proximal end surface with the one or more fingers.

4. The method of claim 1, further comprising:
releasing the arming member to allow the arming member to return to an arming member extended position, and
after releasing the arming member, using the single hand to manually depress the arming member toward the proximal portion of the housing a second time and simultaneously move a stylet hub of the hand-held biopsy device from a stylet hub extended position to a stylet hub armed position.

5. The method of claim 4, further comprising using a finger of the single hand to actuate a stylet hub release, allowing the stylet hub to move from the stylet hub armed position to a stylet hub fired position.

6. The method of claim 5, further comprising, after actuating the stylet hub release, using a same or different finger of the single hand to actuate a cannula hub release, allowing the cannula hub to move from the cannula hub armed position to a cannula hub fired position.

7. The method of claim 6, further comprising removing a core of excised tissue from a stylet coupled to the stylet hub by using an elongate body extending proximally from a pusher disposed in the stylet to advance the pusher distally to dislodge the core of excised tissue from the stylet.

8. The method of claim 6, further comprising removing a core of excised tissue from a stylet coupled to the stylet hub by introducing flushing fluid into an annular space defined by an outer wall of the stylet and an inner wall of a cannula via a flushing port to thereby dislodge the core of excised tissue from the stylet.

* * * * *